(12) United States Patent
Mahmud et al.

(10) Patent No.: US 12,378,562 B2
(45) Date of Patent: Aug. 5, 2025

(54) GADUSOL DERIVATIVE PRODUCTION IN BACTERIA

(71) Applicant: Oregon State University, Corvallis, OR (US)

(72) Inventors: Taifo Mahmud, Corvallis, OR (US); Andrew Robert Osborn, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 20 days.

(21) Appl. No.: 18/354,262

(22) Filed: Jul. 18, 2023

(65) Prior Publication Data

US 2024/0002866 A1 Jan. 4, 2024

Related U.S. Application Data

(62) Division of application No. 17/012,560, filed on Sep. 4, 2020, now Pat. No. 11,739,337.

(60) Provisional application No. 62/897,081, filed on Sep. 6, 2019.

(51) Int. Cl.
*C12N 15/74* (2006.01)
*A61K 8/40* (2006.01)
*A61Q 17/04* (2006.01)

(52) U.S. Cl.
CPC ............... *C12N 15/74* (2013.01); *A61K 8/40* (2013.01); *A61Q 17/04* (2013.01); *A61K 2800/59* (2013.01)

(58) Field of Classification Search
CPC .......... C12N 15/74; C12N 15/76; A61K 8/40; A61K 2800/59; A61Q 17/04
See application file for complete search history.

(56) References Cited

U.S. PATENT DOCUMENTS

2016/0000701 A1 1/2016 Qvit-Raz et al.
2017/0202762 A1 7/2017 Ikeda et al.

FOREIGN PATENT DOCUMENTS

| ES | 2550374 B1 | 9/2016 |
|---|---|---|
| IN | 202017037402 A | 10/2020 |
| WO | 2015174427 A1 | 11/2015 |
| WO | 2019094447 A2 | 5/2019 |

OTHER PUBLICATIONS

ADDGENE plasmid maps for pXP416—retrieved from https://www.addgene.org/26842 on Dec. 29, 2020, 1 page.
ADDGENE plasmid maps for pXP420—retrieved from https://www.addgene.org/26844 on Dec. 29, 2020, 1 page.
Holzwarth, G., "Gadusol Production in *Saccharomyces cerevisiae*", M Sc thesis, Oregon State University, Feb. 27, 2018, 82 pages.
Losantos, et al.; "Rational Design and Synthesis of Efficient Sunscreens to Boost the Solar Protection Factor"; Article; Wiley Online Library, 2017 Wiley-VCH Verlag GmbH & Co. KGaA, Weinheim; Angew. Chem. Int. Ed. 2017; 4 pages (2632-2635).
Osborn et al., "De novo synthesis of a sunscreen compound in vertebrates", eLIFE, 2015, 4:e05919, DOI: 10.7554/eLife.05919.001, May 12, 2015, pp. 1-15.
Shick, et al; "Mycosporine-Like Amino Acids and Related Gadusols: Biosynthesis, Accumulation, and UV-Protective Functions in Aquatic Organisms"; Article; Annu. Rev. Physiol. 2002; 43 pages (223-262).

*Primary Examiner* — Iqbal H Chowdhury
(74) *Attorney, Agent, or Firm* — Schwabe, Williamson & Wyatt, P.C.

(57) ABSTRACT

Disclosed is a synthetic gene cluster for producing gadusol derivatives, expression vectors and host cells containing the same, methods of producing gadusol derivatives, and compositions thereof. In an example, the synthetic gene cluster includes a valA nucleotide sequence capable of expressing ValA protein; a nucleotide sequence capable of expressing methyltransferase/oxidoreductase (MT-Ox) protein; a mysC nucleotide sequence capable of expressing a MysC protein; and a mysD nucleotide sequence capable of expressing a MysD protein. In this way, gadusol derivatives can be produced in amounts sufficient for use in a variety of applications.

19 Claims, 25 Drawing Sheets

Specification includes a Sequence Listing.

Oxybenzone $\lambda_{max}$ = 288, 350 nm

Octinoxate $\lambda_{max}$ = 310 nm

Gadusol $\lambda_{max}$ = 268 nm at pH 2.5

$\lambda_{max}$ = 296 nm at pH 7.0

Prasiolin $\lambda_{max}$ = 324 nm

Shinorine $\lambda_{max}$ = 333 nm

Porphyra-334

$\lambda_{max}$ = 333 nm

Mycosporine-glycine-alanine $\lambda_{max}$ = 333 nm

GADUSOL DERIVATIVE PRODUCTION IN BACTERIA

CROSS REFERENCE TO RELATED APPLICATION

This application is a divisional of U.S. patent application Ser. No. 17/012,560, filed Sep. 4, 2020, which claims the priority benefit of the earlier filing date of U.S. Provisional Application No. 62/897,081, filed Sep. 6, 2019, both of which are hereby incorporated by reference in their entirety.

TECHNICAL FIELD

The present disclosure is in the field of molecular biology and is related to engineered microorganisms and the production of gadusol derivatives by genetically engineered microorganisms.

REFERENCE TO A SEQUENCE LISTING

This application incorporates by reference the Sequence Listing submitted in Computer Readable Form as file 280308 SL, generated on Jul. 31, 2023 and containing 17,894-bytes.

BACKGROUND

Exposure to sun is believed to cause many of the skin changes associated with aging and contributes to pre-cancerous and cancerous skin lesions, benign tumors, wrinkling, mottle pigmentations, and other important challenges to human health and well-being. Despite the wide availability of sun protectant sunscreens and general knowledge of the dangers of too much sun exposure and sun burn, skin cancer rates continue to grow. Furthermore, there is an association between juvenile coral toxicity by oxybenzone and octinoxate, the active ingredients in a wide variety of sunscreen products. Accordingly, there is a need for new, more environmentally-friendly, sunscreen compounds.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 1A shows structures of oxybenzone and octinoxate, synthetic sunscreens that are widely used. FIG. 1B shows structures of gadusol and mycosporine-like amino acids (MAAs);

FIG. 5A depicts predicted chemical structures of gadusporines A, B, and C by nuclear magnetic resonance (NMR) spectroscopy and/or HR-MS. FIG. 5B depicts heteronuclear multiple bond correlations (HMBCs) for gadusporines A and B. FIG. 5C illustrates Marfey's analysis of gadusporine A;

FIG. 6A depicts purification of gadusporine A by preparative HPLC on a Puriflash 450 (Paramus, NJ). FIG. 6B depicts separation of gadusporines B and C from gadusol by semi-preparative HPLC;

DETAILED DESCRIPTION

Figure 1A:
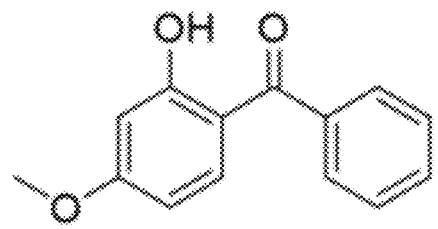
FIGS. 1A-1B depict structures of synthetic and natural sunscreen compounds.
Figure 1A:
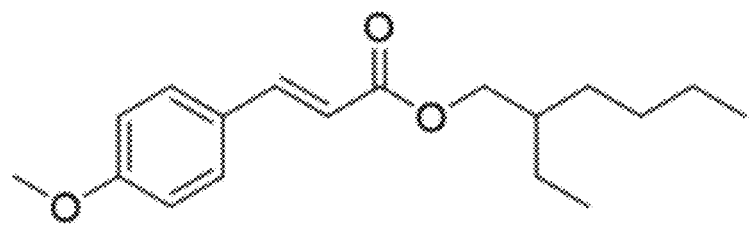

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology,* Greene Publishing Associates, 1992 (and Supplements to 2000); Ausubel et al., *Short Protocols in Molecular Biology: A Compendium of Methods from Current Protocols in Molecular Biology,* 4th ed., Wiley & Sons, 1999. In addition, the materials, methods, and examples are illustrative only and not intended to be limiting.

I. Introduction

Current sunscreen products on the market heavily rely on two synthetic compounds, oxybenzone and octinoxate (FIG. 1A). However, these compounds may be toxic to juvenile coral, and have been banned by the state of Hawaii and the city of Key West, Florida, effective 2021. Oxybenzone concentration in coral reefs varies in Hawaii (0.8-19.2 μg/L) and the US Virgin Islands (75 μg/L-1.4 mg/L), and is within the range of coral toxicity determined experimentally. The toxicity may be due to bleaching and/or induction of phage production. Thus, there exists a need for more environmentally friendly sunscreens.

Figure 1B:
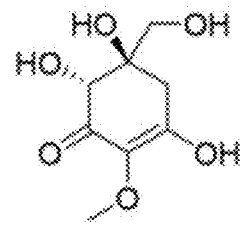
Figure 1B:
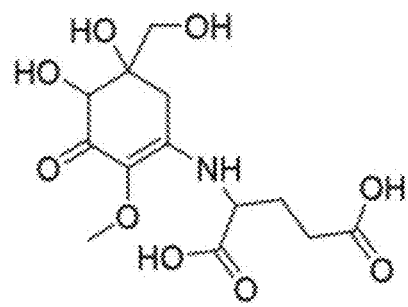
Figure 1B:
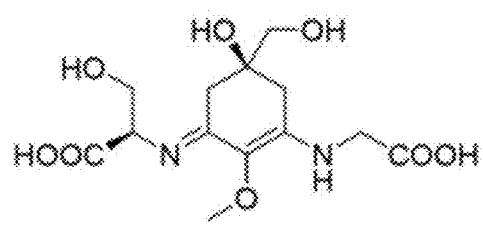
Figure 1B:
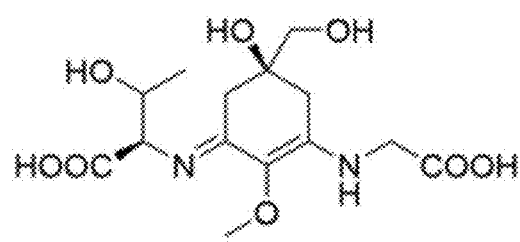
Figure 1B:
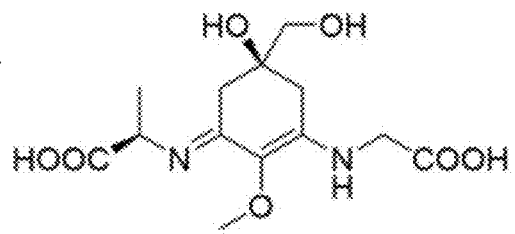

There are some sunscreen compounds that are naturally produced in coral reef environments. Specifically, sunscreen compounds called mycosporine-like amino acids (MAAs) are produced by algae, cyanobacteria, and marine invertebrates. Depicted at FIG. 1B are various structures of MMAs, including prasiolin, shinorine, *porphyra*-334, and mycosporine-glycine-alanine. MAAs also accumulate up the food chain, where they have been identified in the mucus of marine fish in a UV-dependent manner. MAAs may also act as wound healing agents, an activity that would be valuable in a sunscreen product. Most MAAs have a $\lambda_{max} \approx 333$ nm, which is on the lower end of the UV-A range (310-400 nm). Some MAAs, such as palythene and usujirene, $\lambda_{max}$ at 360 nm and 357 nm respectively, do absorb at higher in the UV-A range, however their biosynthesis is not well understood.

Figure 2:
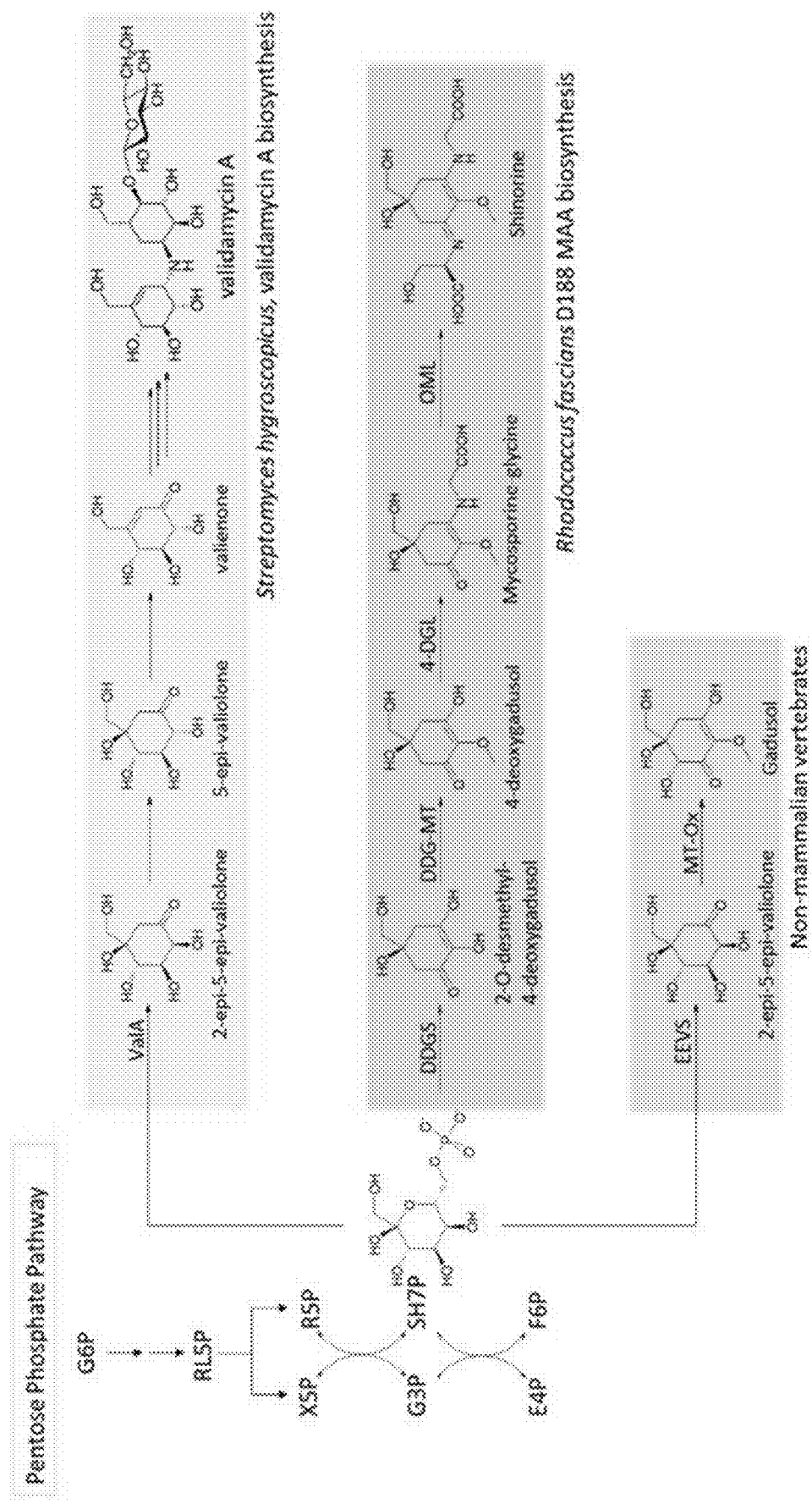
FIG. 2 depicts pathways to gadusol, MAAs, and valA.

MAAs are typically produced in small amounts by the producing organisms, hampering their exploitation as safe alternatives to currently used commercial products. Recently, their biosynthesis has been extensively explored by heterologous expression, leading to novel MAA production and high yields. MAA biosynthesis starts with a 2-O-desmethyl-4-deoxygadusol synthase (DDGS), encoded by the mysA gene, catalyzing the cyclization of sedoheptulose 7-phosphate (SH7P) to 2-O-desmethyl-4-deoxygadusol, followed by methylation by an O-methyltransferase (O-MT) (mysB) to form 4-deoxygadusol (4-DG) (FIG. 2). All MAA gene clusters encode an ATP-grasp ligase like enzyme (mysC) that attaches an amino acid (usually glycine) to 4-DG to form an oxomycosporine. Fungi only have these three genes whereas other organisms (algae, bacteria, and marine invertebrates) have a fourth gene, mysD, which attaches a second amino acid, forming an MAA. Most organisms contain a D-Ala D-Ala ligase-like gene in their genome, also from the ATP grasp family, to perform this final step. However, some organisms like *Anabaena variabilis*, encode a NRPS-like gene instead. These enzymes show promiscuity by adding different amino acids to the 4-DG core, leading to the production of many different MAAs. This is highlighted by the heterologous expression of MAAs in *Streptomyces avermitilis*, where shinorine, *porphyra*-334, and a MAA mycosporine-glycine-alanine can be produced (see FIG. 1B and FIG. 2). This flexibility is not limited to lab conditions, as MAAs are often found as a mixture of compounds from natural sources. The last three enzymes in MAA biosynthesis are usually referred to by their homology to O-MT, ATP-grasp, and D-Ala D-Ala ligase enzymes.

Herein these enzymes are named according to their actual function as 2-O-desmethyl-4-deoxygadusol methyltransferase (DDG-MT), 4-deoxygadusol ligase (4-DGL), and oxomycosporine ligase (OML), respectively.

In addition to MAAs, the structurally related sunscreen compound gadusol (see FIG. 1B and FIG. 2) may also be found in marine environments. Gadusol was first identified in the roes of Atlantic cod and initially thought to be acquired through the diet due to its similarity to the core structure of MAAs. However, using zebrafish as a model, it has been established that gadusol can be produced by fish themselves. Gadusol genes have been found in coral reef fish, and gadusol has been identified in eggs of *Dicentrarchus labrax* (European Sea Bass). Amphibians, birds, and reptiles may also produce gadusol.

Gadusol is biosynthesized by two enzymes, a 2-epi-5-epi-valiolone synthase (EEVS) (related to the DDGS in MAA biosynthesis) and a methyltransferase-oxidoreductase (MT-Ox). The EEVS cyclizes SH7P into 2-epi-5-epi-valiolone (EEV). The MT-Ox then methylates and oxidizes EEV to form gadusol (FIG. 2). Gadusol has a UV absorbance maxima of 296 nm at pH 7.0 or 268 nm at pH 2.5. Gadusol has antioxidant activity as well. The presence of EEVSs in vertebrate genomes was unexpected since EEVSs and other sugar phosphate cyclases (SPCs) are thought to descend from the shikimate pathway enzyme 3-dehydroquinate synthase, which vertebrates lack. Some algae also contain the gadusol biosynthetic genes, suggestive of a horizontal gene transfer event from an alga to a vertebrate ancestor. Gadusol biosynthesis is the only known pathway where an EEVS is used to form a sunscreen. EEVS enzymes are usually found in aminocyclitol biosynthetic gene clusters, for example acarbose and validamycin A. On the other hand, DDGSs are only found in MAA gene clusters, highlighting a major difference between the distribution of these two closely related proteins.

Despite the similarity between 4-DG and gadusol, just one molecule has been identified where gadusol appears to replace 4-DG as an MAA core; the compound prasiolin (see FIG. 11B), produced by the terrestrial green alga *Prasiola calophylla*. Prasiolin has a gadusol core with glutamic acid attached to it, thus is an analog of mycosporine-glycine. Prasiolin has a unique UV absorbance with $\lambda_{max}$=324 nm, whereas other oxomycosporines typically have $\lambda_{max}$≈310 nm. However, it is not clear if the core structure of prasiolin is directly derived from gadusol or from 4-DG or if the product subsequently undergoes post assembly hydroxylation.

In the present disclosure, an interkingdom genetic mix-and-match approach is disclosed for production of MAA analogs similar to prasiolin. These compounds, termed gadusporines, show unique UV absorbance at 340 nm, expanding the range of mycosporine and gadusol-based sunscreen products. The interkingdom genetic mix-and-match approach relies on use of assorted genes from a vertebrate (zebrafish) and two Gram-(+) bacteria, *Streptomyces hygroscopicus* subsp. *jinggangensis* (a validamycin producer) and *Rhodococcus fascians* (a plant pathogen). The genes are expressed in a well-established heterologous expression system *Streptomyces coelicolor* A(3)2.

II. Overview of Several Embodiments

The present disclosure provides a synthetic gene cluster, expression vectors, genetically-engineered microorganisms and methods for the production of gadusol derivatives. The gadusol derivatives produced by the engineered microorganisms and methods disclosed herein may be useful as a UV protectant (e.g., sunscreen), and as such the present disclosure contributes significantly to improvement of human health and well-being. The engineered microorganisms present a new avenue for large-scale production of one or more UV protectants for possible commercial and clinical uses. Large-scale production allows for the use of gadusol derivatives in pharmaceuticals, formulations, cosmetics, or even dietary formulations and products. By way of example, formulations may include pills/capsules, creams, lotions, or the like.

In one exemplary embodiment, a synthetic gene cluster includes one or more of a valA nucleotide sequence capable of expressing ValA, a nucleotide sequence capable of expressing methyltransferase/oxidoreductase (MT-Ox) protein, a mysC nucleotide sequence capable of expressing a MysC protein, and a mysD nucleotide sequence capable of expressing a MysD protein.

In another exemplary embodiment, an expression vector with a synthetic gene cluster comprises one or more of a valA nucleotide sequence capable of expressing ValA, a nucleotide sequence capable of expressing methyltransferase/oxidoreductase (MT-Ox) protein, a mysC nucleotide sequence capable of expressing a MysC protein, and a mysD nucleotide sequence capable of expressing a MysD protein.

Another exemplary embodiment includes a host cell with an expression vector with a synthetic gene cluster comprising one or more of a valA nucleotide sequence capable of expressing ValA, a nucleotide sequence capable of expressing methyltransferase/oxidoreductase (MT-Ox) protein, a mysC nucleotide sequence capable of expressing a MysC protein, and a mysD nucleotide sequence capable of expressing a MysD protein.

In another exemplary embodiment, disclosed is a bacterium with an expression vector with a synthetic gene cluster comprising one or more of a valA nucleotide sequence capable of expressing ValA, a nucleotide sequence capable of expressing methyltransferase/oxidoreductase (MT-Ox) protein, a mysC nucleotide sequence capable of expressing a MysC protein, and a mysD nucleotide sequence capable of expressing a MysD protein.

In another exemplary embodiment, a method of producing one or more gadusol derivatives comprises culturing a host cell having an expression vector with a synthetic gene cluster. The synthetic gene cluster may comprise one or more of a valA nucleotide sequence capable of expressing ValA, a nucleotide sequence capable of expressing methyltransferase/oxidoreductase (MT-Ox) protein, a mysC nucleotide sequence capable of expressing a MysC protein, and a mysD nucleotide sequence capable of expressing a MysD protein. The method may further include isolating one or more of the gadusol derivatives from the culture.

Another exemplary embodiment comprises a sunscreen compound having one of the following structures:

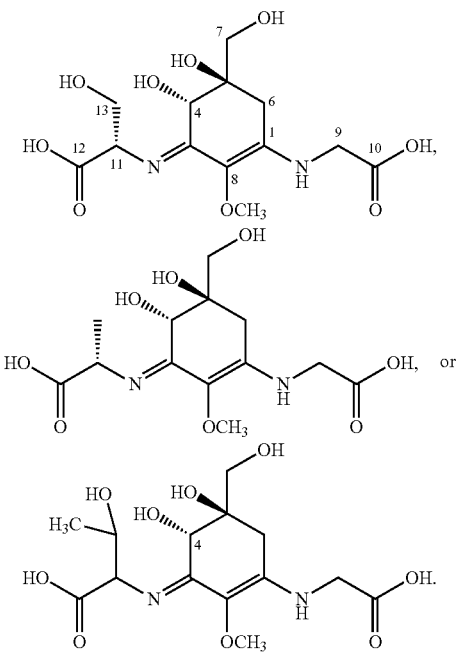

Yet another exemplary embodiment includes a sunscreen composition, comprising one or more of the following compounds:

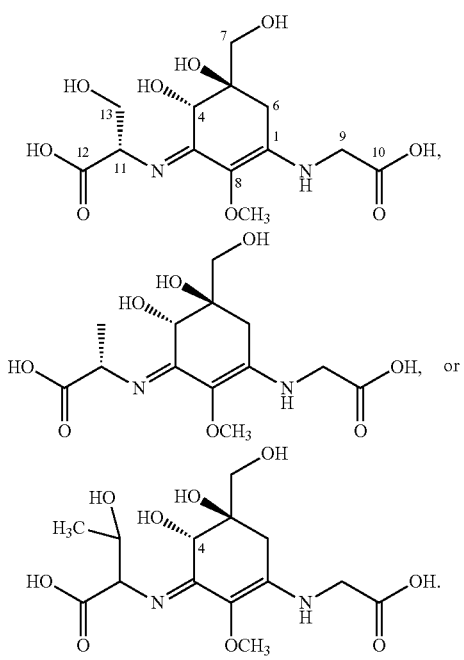

III. Terms

In order to facilitate review of the various embodiments of this disclosure, the following explanations of specific terms are provided:

Amplification: When used in reference to nucleic acids, techniques that increase the number of copies of a nucleic acid molecule in a sample or specimen. An example of amplification is the polymerase chain reaction (PCR), in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744, 311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427, 930); coupled ligase detection and PCR (see U.S. Pat. No. 6,027,889); and NASBA™ RNA transcription-free amplification (see U.S. Pat. No. 6,025,134).

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, and/or a change in ionization. Structural analogs are often found using quantitative structure activity relationships (QSAR), with techniques such as those disclosed in Remington (*The Science and Practice of Pharmacology*, 19th Edition (1995), chapter 28). When the changes to the original compound are substantial, or many incremental changes are combined, the compound is no longer an analog. A derivative is a biologically active molecule derived from the base structure. A mimetic is a molecule that mimics the activity of another molecule by mimicking the structure of such a molecule, such as a biologically active molecule. Thus, the term "mimetic" indicates a definite structure related to activity.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Conservative substitution: Amino acid substitutions that do not substantially alter the activity (specificity or binding affinity) of the molecule. Typically conservative amino acid substitutions involve substitutions of one amino acid for another amino acid with similar chemical properties (e.g., charge or hydrophobicity). Table 1 shows exemplar conservative amino acid substitutions:

TABLE 1

| Conservative amino acid substitutions | |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

DNA (deoxyribonucleic acid): A long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Expression: Refers to the transcription and translation of an endogenous gene or a transgene in a host cell. For example, in the case of antisense constructs, expression may refer to the transcription of the antisense DNA only. In addition, expression refers to the transcription and stable accumulation of sense (mRNA) or functional RNA. Expression may also refer to the production of protein.

Functional fragments and variants of a polypeptide: Included are fragments and variants that maintain one or more functions of the parent polypeptide. It is recognized that the gene or cDNA encoding a polypeptide can be considerably mutated without materially altering one or more the polypeptide's functions. First, the genetic code is degenerate, and thus different codons encode the same amino acids. Second, even where an amino acid substitution is introduced, the mutation can be conservative and have no material impact on the essential function(s) of a protein. Third, part of a polypeptide chain can be deleted without impairing or eliminating all of its functions. Fourth, insertions or additions can be made in the polypeptide chain for example, adding epitope tags, without impairing or eliminating its functions.

Other modifications that can be made without materially impairing one or more functions of a polypeptide include, for example, in vivo or in vitro chemical and biochemical modifications or the incorporation of unusual (e.g., unnatural) amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. A variety of methods for labeling polypeptides, and labels useful for such purposes, include radioactive isotopes such as $^{32}P$, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, 200, or even more amino acid residues.

Gene: Refers to any segment of nucleic acid associated with a biological function. Thus, genes include coding sequences and/or the regulatory sequences required for their expression. For example, "gene" refers to a nucleic acid fragment that expresses mRNA, or specific protein, including regulatory sequences. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

Gene Cluster: A set of genetic elements grouped together on the chromosome, the protein products of which have a related function, such as forming a product biosynthetic pathway.

Heterologous: As it relates to nucleic acid sequences such as coding sequences and control sequences, "heterologous" denotes sequences that are not normally associated with a region of a recombinant construct, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different than the native gene). Similarly, a host cell transformed with a construct which is not normally present in the host cell would be considered heterologous for purposes of this disclosure.

Homologous amino acid sequence: Any polypeptide which is encoded, in whole or in part, by a nucleic acid sequence that hybridizes to any portion of the coding region nucleic acid sequences. A homologous amino acid sequence is one that differs from an amino acid sequence shown in the sequence listing by one or more conservative amino acid substitutions. Such a sequence also encompasses allelic variants (defined above) as well as sequences containing deletions or insertions which retain the functional characteristics of the polypeptide. Preferably, such a sequence is at least 75%, more preferably 80%, more preferably 85%, more preferably 90%, more preferably 95%, and most preferably 98% identical to any one of the amino acid sequences.

Homologous amino acid sequences include sequences that are identical or substantially identical to the amino acid sequences of the sequence listing. By "amino acid sequence substantially identical" it is meant a sequence that is at least 90%, preferably 95%, more preferably 97%, and most preferably 99% or 100% identical to an amino acid sequence of reference and that preferably differs from the sequence of reference by a majority of conservative amino acid substitutions. Consistent with this aspect of the invention, polypeptides having a sequence homologous to any one of the amino acid sequences of the sequence listing include naturally-occurring allelic variants, as well as mutants or any other non-naturally occurring variants that retain the inherent characteristics of any polypeptide of the sequences disclosed herein.

Homology can be measured using sequence analysis software such as Sequence Analysis Software Package of the Genetics Computer Group, University of Wisconsin Biotechnology Center, 1710 University Avenue, Madison, WI 53705. Amino acid sequences can be aligned to maximize identity. Gaps can also be artificially introduced into the sequence to attain optimal alignment. Once the optimal alignment has been set up, the degree of homology is established by recording all of the positions in which the amino acids of both sequences are identical, relative to the total number of positions. Homologous polynucleotide sequences are defined in a similar way. Preferably, a homologous sequence is one that is at least 45%, 50%, 60%, 70%, 75%, 80%, 85%, 86%, 87%, 88%, 89%, 90%, 91%, 92%, 93%, 94%, 95%, 96%, 97%, 98%, 99% or identical to any one of the coding sequences.

Hydroxyl or Hydroxy: —OH

Isolated: An isolated biological component (such as a nucleic acid molecule or protein) is one that has been substantially separated or purified away from other biological components in the cell of the organism in which the component naturally occurs, such as other chromosomal and extra-chromosomal DNA and RNA, proteins and organelles. With respect to nucleic acids and/or polypeptides, the term can refer to nucleic acids or polypeptides that are no longer flanked by the sequences typically flanking them in nature. Nucleic acids and proteins that have been isolated include nucleic acids and proteins purified by standard purification methods. The term also embraces nucleic acids and proteins prepared by recombinant expression in a host cell as well as chemically synthesized nucleic acids.

Mutation: Refers to an insertion, deletion or substitution of one or more nucleotide bases of a nucleic acid sequence, so that the nucleic acid sequence differs from the wild-type sequence. For example, a 'point' mutation refers to an alteration in the sequence of a nucleotide at a single base position from the wild type sequence.

Nucleic acid molecule: Refers to a polymer of DNA or RNA that can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

Operably linked: A first nucleic acid sequence is operably linked with a second nucleic acid sequence when the first nucleic acid sequence is placed in a functional relationship with the second nucleic acid sequence (e.g., joined as part of the same nucleic acid molecule, suitably positioned and oriented for transcription to be initiated from the promoter). For instance, a promoter is operably linked to a coding sequence if the promoter affects the transcription or expression of the coding sequence. Generally, operably linked DNA sequences are contiguous and, where necessary to join two protein-coding regions, in the same reading frame. DNA operably linked to a promoter is under transcriptional initiation regulation of the promoter. Coding sequences can be operably-linked to regulatory sequences in sense or antisense orientation.

Ortholog: Two nucleic acid or amino acid sequences are orthologs of each other if they share a common ancestral sequence and diverged when a species carrying that ancestral sequence split into two species. Orthologous sequences are also homologous sequences.

Overexpression: Refers to the level of expression in transgenic cells or organisms that exceeds levels of expression in corresponding normal or untransformed cells or organisms.

Probes and primers: Nucleic acid probes and primers can be readily prepared based on the nucleic acid molecules provided in this disclosure. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides, 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, CA, 1990). PCR primer pairs can be derived from a known sequence, for example, by using computer programs intended for that purpose such as Primer (Version 0.5, © 1991, Whitehead Institute for Biomedical Research, Cambridge, MA). The specificity of a particular probe or primer increases with its length. Thus, in order to obtain greater specificity, probes and primers can be selected that comprise at least 17, 20, 23, 25, 30, 35, 40, 45, 50 or more consecutive nucleotides of desired nucleotide sequence.

Promoter: Refers to a nucleotide sequence, for example upstream (5') to its coding sequence, which controls the expression of the coding sequence by providing the recognition for RNA polymerase and other factors required for proper transcription. An "inducible promoter" is a regulated promoter that can be turned on in a cell by an external stimulus, such as a chemical, light, hormone, stress, or a pathogen.

Protein, peptide, and polypeptide: A peptide is two or more amino acids joined together by peptide bonds, and a polypeptide is a chain of any number of amino acids. A protein contains one or more polypeptides, and are thus long chains of amino acids connected via peptide bods. The terms "protein", "peptide" and "polypeptide" are used interchangeably herein.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. "Recombinant" also is used to describe nucleic acid molecules that have been artificially manipulated, but contain the same control sequences and coding regions that are found in the organism from which the gene was isolated.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.,* 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, MD) and on the Internet, for use in connection with the sequence-analysis programs blastp, blastn, blastx, tblastn and tblastx. A description of how to determine sequence identity using this program is available on the internet under the help section for BLAST™.

For comparisons of amino acid sequences of greater than about 30 amino acids, the "Blast 2 sequences" function of the BLAST™ (Blastp) program is employed using the default BLOSUM62 matrix set to default parameters (cost to open a gap [default=5]; cost to extend a gap [default=2]; penalty for a mismatch [default=−3]; reward for a match [default=1]; expectation value (E) [default=10.0]; word size [default=3]; number of one-line descriptions (V) [default=100]; number of alignments to show (B) [default=100]). When aligning short peptides (fewer than around 30 amino acids), the alignment should be performed using the Blast 2 sequences function, employing the PAM30 matrix set to default parameters (open gap 9, extension gap 1 penalties). Proteins (or nucleic acids) with even greater similarity to the reference sequences will show increasing percentage identities when assessed by this method, such as at least 50%, at least 60%, at least 70%, at least 80%, at least 85%, at least 90%, or at least 95% sequence identity.

For comparisons of nucleic acid sequences, the "Blast 2 sequences" function of the BLAST™ (Blastn) program is employed using the default BLOSUM62 matrix set to default parameters (cost to open a gap [default=11]; cost to extend a gap [default=1]; expectation value (E) [default=10.0]; word size [default=11]; number of one-line descriptions (V) [default=100]; number of alignments to show (B) [default=100]). Nucleic acid sequences with even greater similarity to the reference sequences will show increasing percentage identities when assessed by this method, such as at least 60%, at least 70%, at least 75%, at least 80%, at least 85%, at least 90%, at least 95%, or at least 98% sequence identity. An alternative indication that two nucleic acid molecules are closely related is that the two molecules hybridize to each other under stringent conditions.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Transfection: A process by which a nucleic acid molecule is introduced into cell, for instance by molecular biology techniques, resulting in a transfected (or transformed) cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Transformed: A transformed cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

As used herein, a "transgenic", "transformed", or "recombinant" cell refers to a genetically modified or genetically altered cell, the genome of which comprises a recombinant DNA molecule or sequence ("transgene"). For example, a "transgenic cell" can be a cell transformed with a "vector." A "transgenic", "transformed", or "recombinant" cell thus refers to a host cell such as yeast cell into which a heterologous nucleic acid molecule has been introduced. The nucleic acid molecule can be stably integrated into the genome by methods generally known in the art. For example, "transformed," "transformant," and "transgenic" cells have been through the transformation process and contain a foreign or exogenous gene. The term "untransformed" refers to cells that have not been through the transformation process.

The term "transformation" refers to the transfer of a nucleic acid fragment into the genome of a host cell, or the transfer into a host cell of a nucleic acid fragment that is maintained extrachromosomally. A "transgene" refers to a gene that has been introduced into the genome by transformation. Transgenes may include, for example, genes that are heterologous or endogenous to the genes of a particular cell to be transformed. Additionally, transgenes may comprise native genes inserted into a non-native organism, or chimeric genes. The term "endogenous gene" refers to a native gene in its natural location in the genome of an organism. Such genes can be hyperactivated in some cases by the introduction of an exogenous strong promoter into operable association with the gene of interest. A "foreign" or an "exogenous" gene refers to a gene not normally found in the host cell but that is introduced by gene transfer.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses. A plasmid is a vector.

"Vector" is defined to include, inter alia, any plasmid, cosmid, phage or other construct in double or single stranded linear or circular form that may or may not be self-transmissible or mobilizable, and that can transform prokaryotic or eukaryotic host either by integration into the cellular genome or exist extrachromosomally, e.g., autonomous replicating plasmid with an origin of replication. A vector can comprise a construct such as an expression cassette having a DNA sequence capable of directing expression of a particular nucleotide sequence in an appropriate host cell, comprising a promoter operably linked to the nucleotide sequence of interest that also is operably linked to termination signals. An expression cassette also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus.

Wild type: Refers to an untransformed cell, i.e., one where the genome has not been altered by the presence of the recombinant DNA molecule or sequence or by other means of mutagenesis. A "corresponding" untransformed cell is a typical control cell, i.e., one that has been subjected to transformation conditions, but has not been exposed to exogenous DNA. In addition, a "wild type" gene refers to a gene, e.g., a recombinant gene, with its original or native DNA sequence, in contrast to a "mutant" gene.

IV. Synthetic Gene Clusters, Expression Vectors, Genetically-Engineered Microorganisms, Methods for the Production of Gadusol Derivatives, Compounds, and Compositions i. Synthetic Gene Clusters As disclosed herein, a synthetic gene cluster may include one or more of a valA nucleotide sequence capable of expressing ValA, a nucleotide sequence capable of expressing methyltransferase/oxidoreductase (MT-Ox) protein, a mysC nucleotide sequence capable of expressing a MysC protein, and a mysD nucleotide sequence capable of expressing a MysD protein.

In an example, the valA nucleotide sequence is from *Streptomyces hygroscopicus*, and encodes for example a ValA protein that is a least 95% identical to SEQ ID NO: 6, such as at least 95%, 96%, 97%, 98%, 99%, or even 100% identical. In embodiments, the nucleic acid sequence encoding the ValA protein comprises a nucleic acid sequence at least 95% identical to SEQ ID NO: 2, such as at least 95%, 96%, 97%, 98% 99% or even 100% identical.

In another additional or alternative example, the MT-Ox nucleotide sequence is from *Danio rerio* (drMT-Ox), and encodes a protein that is a least 95% identical to SEQ ID NO: 7, such as at least 95%, 96%, 97%, 98%, 99%, or even 100% identical. In embodiments, the nucleic acid sequence encoding the drMT-Ox protein comprises a nucleic acid sequence at least 95% identical to SEQ ID NO: 3, such as at least 95%, 96%, 97%, 98% 99% or even 100% identical.

In another additional or alternative example, the mysC nucleotide sequence is from *Rhodococcus fascians* D188, and encodes a protein that is a least 95% identical to SEQ ID NO: 8, such as at least 95%, 96%, 97%, 98%, 99%, or even 100% identical. In embodiments, the mysC nucleotide sequence is a least 95% identical to SEQ ID NO: 4, such as at least 95%, 96%, 97%, 98%, 99%, or even 100% identical.

In another additional or alternative example, the mysD nucleotide sequence is from *Rhodococcus fascians* D188, and encodes a protein that is a least 95% identical to SEQ ID NO: 9, such as at least 95%, 96%, 97%, 98%, 99%, or even 100% identical. In embodiments, the mysD nucleotide sequence is a least 95% identical to SEQ ID NO: 5, such as at least 95%, 96%, 97%, 98%, 99%, or even 100% identical.

ii. Expression Vectors

Further disclosed is an expression vector comprising the synthetic gene cluster as described herein. Exemplary nucleic acids including sequences encoding the genes of the gene cluster disclosed herein (e.g., valA, drMT-Ox, mysC and/or mysD) can be prepared by cloning techniques (see Example 1 below). Examples of appropriate cloning and sequencing techniques, and instructions sufficient to direct persons of skill through cloning are found in Sambrook et al. (in *Molecular Cloning: A Laboratory Manual*, CSHL, New York, 1989) and Ausubel et al. (In *Current Protocols in Molecular Biology*, Greene Publ. Assoc. and Wiley-Intersciences, 1992). Product information from manufacturers of biological reagents and experimental equipment also provide useful information. Such manufacturers include the SIGMA Chemical Company (Saint Louis, MO), R&D Systems (Minneapolis, MN), Pharmacia Amersham (Piscataway, NJ), CLONTECH Laboratories, Inc. (Palo Alto, CA), Chem Genes Corp., Aldrich Chemical Company (Milwaukee, WI), Glen Research, Inc., GIBCO BRL Life Technologies, Inc. (Gaithersburg, MD), Fluka Chemica-Biochemika Analytika (Fluka Chemie AG, Buchs, Switzerland), Invitrogen (San Diego, CA), and Applied Biosystems (Foster City, CA), as well as many other commercial sources known to one of skill.

The following provides representative techniques for preparing a protein-encoding nucleic acid molecule. RNA or DNA is extracted from cells by any one of a variety of methods well known to those of ordinary skill in the art. Sambrook et al. (In Molecular Cloning: A Laboratory Manual, Cold Spring Harbor Laboratory Press, New York, 1989) and Ausubel et al. (In Current Protocols in Molecular Biology, Greene Publ. Assoc, and Wiley-Intersciences, 1992) provide representative descriptions of methods for RNA or DNA isolation. Representative methods and conditions for RT-PCR are described by Kawasaki et al. (In PCR Protocols, A Guide to Methods and Applications, Innis et al. (eds.) 21-27 Academic Press, Inc., San Diego, California, 1990). The selection of amplification primers will be made according to the portion(s) of the DNA that is to be amplified. In one embodiment, primers may be chosen to amplify a segment of a DNA molecule (e.g., a specific ORF or set of adjacent ORFs, with or without regulatory sequences, or regulatory sequences alone) or, in another embodiment, the entire DNA molecule. Variations in amplification conditions may be required to accommodate primers and amplicons of differing lengths and composition; such considerations are well known in the art and are discussed for instance in Innis et al. (PCR Protocols, A Guide to Methods and Applications, Academic Press, Inc., San Diego, CA, 1990). It will be appreciated that many different primers may be derived from the provided nucleic acid sequences. In addition, both conventional hybridization and PCR amplification procedures may be utilized to clone sequences encoding orthologs. Orthologs will generally share sequence identity with the nucleic acid sequences so that the primary functions of the proteins, are maintained.

The choice of the expression system will be influenced by the features desired for the expressed polypeptides. Any transducible cloning vector can be used as a cloning vector for the nucleic acid constructs presently disclosed. If large clusters are to be expressed, it is preferable that phagemids, cosmids, PIs, yeast artificial chromosomes (YACs), bacterial artificial chromosomes (BACs), P1 artificial chromosomes (PACs), human artificial chromosomes (HACs), mammalian artificial chromosomes (MACs), or similar cloning vectors are used for cloning the nucleotide sequences into the host cell and subsequent expression. These vectors are advantageous due to their ability to insert and stably propagate larger fragments of DNA, compared to MI3 phage and lambda phage.

In an embodiment, one or more of the disclosed ORFs and/or variants thereof can be inserted into one or more expression vectors, using methods known to those of skill in the art. Vectors are used to introduce a synthetic gene cluster of the present disclosure into host cells either integrated or episomal. Prokaryotic host cells or other host cells with rigid cell walls may be transformed using any method known in the art, including, for example, calcium phosphate precipitation, electroporation, and the like.

Representative prokaryote transformation techniques are described in Dower (Genetic Engineering, Principles and Methods, 12: 275-296, Plenum Publishing Corp., 1990) and Hanahan et al. (Methods EnzymoL, 204: 63, 1991). Vectors may include one or more expression control sequences operably linked to the desired ORF(s). However, the choice of an expression cassette may depend upon the host system selected and features desired for the expressed polypeptide or natural product. Typically, the expression cassette includes a promoter that is functional in the selected host system and can be constitutive or inducible. In an embodiment, the expression cassette includes for each ORF a promoter, ribosome binding site, a start codon (ATG) if necessary, and optionally a region encoding a leader peptide in addition to the desired DNA molecule and stop codon. In addition, a 3' terminal region (translation and/or transcription terminator) can be included within the cassette. The ORF constituted in the DNA molecule may be solely controlled by the promoter so that transcription and translation occur in the host cell. Promoter encoding regions are well known and available to those of skill in the art. Examples of promoters include control sequences, bacterial promoters (such as those derived from sugar metabolizing enzymes, such as galactose, lactose and maltose), promoter sequences derived from biosynthetic enzymes such as tryptophan, the beta-lactamase promoter system, bacteriophage lambda PL and TF and viral promoters.

The presence of additional regulatory sequences within the expression cassette may be desirable to allow for regulation of expression of the one or more ORFs relative to the growth of the host cell. These regulatory sequences are well known in the art.

The polynucleotide sequences encoding the genes of the gene cluster disclosed can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host cell are known in the art. In one example, the expression vector is pTMAO-G3. In an example, the expression vector includes any iteration of the synthetic gene cluster described above at IV(i).

In an example, an expression vector with a synthetic gene cluster comprises a valA nucleotide sequence capable of expressing ValA; a nucleotide sequence capable of expressing methyltransferase/oxidoreductase (MT-Ox) protein; a mysC nucleotide sequence capable of expressing a MysC protein; and a mysD nucleotide sequence capable of expressing a MysD protein. The expression vector may be pTMAO-G3.

iii. Host Cells Including an Expression Vector with a Synthetic Gene Cluster

Disclosed herein are host cells including an expression vector with a synthetic gene cluster of the present disclosure. Specifically, the synthetic gene cluster may comprise one or more of a valA nucleotide sequence capable of expressing ValA, a nucleotide sequence capable of expressing methyltransferase/oxidoreductase (MT-Ox) protein, a mysC nucleotide sequence capable of expressing a MysC protein, and a mysD nucleotide sequence capable of expressing a MysD protein. In an example, the expression vector included in the host cell is pTMAO-G3. In an example, the expression vector comprises any iteration of the synthetic gene cluster described above at IV(i).

Host cells of the present disclosure include mammalian cells (e.g., HEK293, CHO, etc.), insect cells (e.g., Sf9, Sf21, etc.), yeast cells (e.g., *Saccharomyces cerevisiae*), bacterial cells (e.g., *E. Coli, Streptomyces*, etc.), fungal cells (e.g., *Aspergillus oryzae, Aspergillus fumigatus*, etc.), and algal cells. It is also within the scope of this disclosure to produce one or more gadusol derivatives via the expression vector with the synthetic gene cluster using cell-free methodology.

In one example, the host cell comprises a bacterial cell. For example, the host cell may comprise a *Streptomyces coelicolor* (*S. coelicolor*) cell. Accordingly, disclosed herein is a bacterium with an expression vector including a synthetic gene cluster comprising a valA nucleotide sequence capable of expressing ValA, a nucleotide sequence capable of expressing methyltransferase/oxidoreductase (MT-Ox) protein, a mysC nucleotide sequence capable of expressing a MysC protein, and a mysD nucleotide sequence capable of expressing a MysD protein. As one example, the bacterium has the accession number PTA-126147.

iv. Methods for Production of Gadusol Derivatives

As disclosed herein, a method of producing one or more gadusol derivatives (e.g., gadusporine A, gadusporine B, gadusporine C) includes culturing a host cell that includes a synthetic gene cluster as disclosed herein, followed by isolating the one or more gadusol derivatives from the culture. Generally, the method includes culturing a recombinant microorganism harboring a disclosed gene cluster at a sufficient temperature under sufficient conditions and for a sufficient period of time to allow for the production of gadusol derivatives. Preferably, the temperature is adjusted to match the optimal temperature for the type of microorganism being used.

In some embodiments, a starter culture may be used. The starter culture may be used to inoculate a larger volume of the same or similar medium that is then cultured at an appropriate temperature for a period of time sufficient for maximum production of gadusol derivatives. By way of example, the engineered microorganism may be cultured up to 5 days, although greater or lesser periods of culture are within the scope of this disclosure.

v. Compounds of the Present Disclosure

Disclosed herein are compounds expressed via the synthetic gene clusters harbored by their respective host cells (e.g., *S. coelicolor*). The compounds encompassed by the present disclosure include any and all compounds that are capable of being produced via the synthetic gene clusters herein disclosed, harbored by any of the host cells herein disclosed or otherwise available for use as expression systems. The compounds encompassed by the present disclosure may be understood to in some examples comprise derivatives of gadusol (FIG. 2).

Figure 5A:
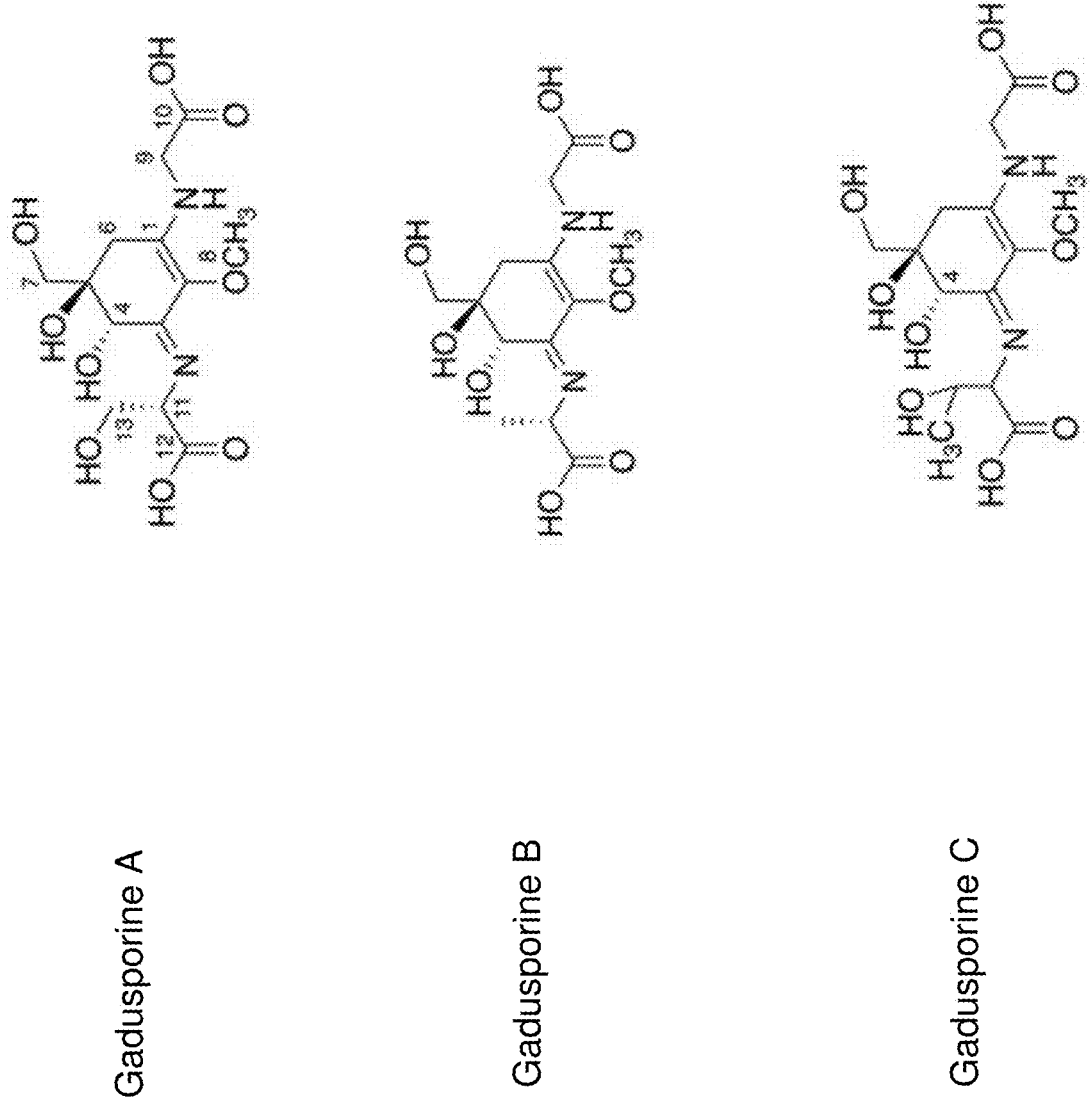
FIGS. 5A-5C illustrate structural elucidation of gadusporines.

As one example, a compound of the present disclosure comprises the following structure:

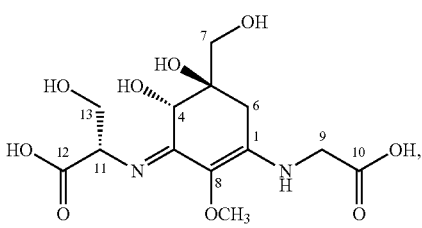 [SMILES: COC1=C(NCC(=O)O)C[C@@](O)(CO)[C@@H](O)/C1=N\[C@@H](CO)C(=O)O]

and herein is termed gadusporine A ((S)-2-(((5R,6S,E)-3-((carboxymethyl)amino)-5,6-dihydroxy-5-(hydroxymethyl)-2-methoxycyclohex-2-en-1-ylidene)amino)-3-hydroxypropanoic acid) (FIG. 5A).

As another example, a compound of the present disclosure comprises the following structure:

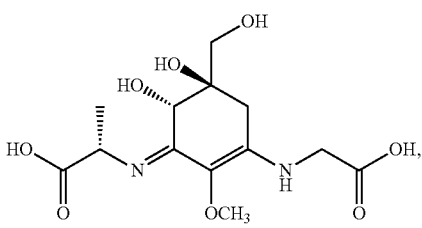

and herein is termed gadusporine B ((S)-2-(((5R,6S,E)-3-((carboxymethyl)amino)-5,6-dihydroxy-5-(hydroxymethyl)-2-methoxycyclohex-2-en-1-ylidene)amino)propanoic acid (FIG. 5A).

As another example, a compound of the present disclosure comprises the following structure:

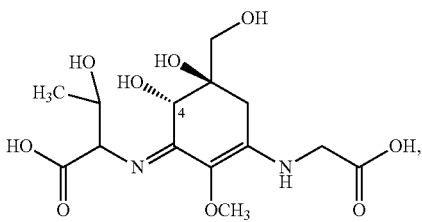 [SMILES: COC1=C(NCC(=O)O)C[C@@](O)(CO)[C@@H](O)/C1=N\C(C(=O)O)C(C)O]

and herein is termed gadusporine C (2-(((5R,6S,E)-3-((carboxymethyl)amino)-5,6-dihydroxy-5-(hydroxymethyl)-2-methoxycyclohex-2-en-1-ylidene)amino)-3-hydroxybutanoic acid) (FIG. 5A).

vi. Compositions

Disclosed herein are compositions (e.g., cosmetic and personal care compositions, such as sunscreen compositions) that include at least one or more of gadusporine A, gadusporine B and gadusporine C. Cosmetic and personal care compositions relevant to the present disclosure include but are not limited to skin lotions and creams, skin gels, serums and liquids, facial and body cleansing products, wipes, liquid and bar soap, color cosmetic formulations, make-ups, foundations, sun care products, sunscreens, sunless tanning formulations, shampoos, conditioners, hair color formulations, hair relaxers, products with alpha hydroxy acid (AHA) and beta hydroxy acid (BHA) and hair fixatives such as sprays, gels, mousses, pomades, and waxes, including low VOC hair fixatives and sunscreens. These cosmetic and personal care compositions may be in any form, including without limitation, emulsions, gels, liquids, sprays, solids, mousses, powders, wipes, or sticks.

In a representative embodiment, the composition is a sunscreen composition. The sunscreen composition may include at least one sunscreen agent. For example, the sunscreen compositions of the present disclosure may include at least one sunscreen agent including but not limited to gadusporine A, gadusporine B, and gadusporine C. The sunscreen compositions of the present disclosure may additionally or alternatively include one or more other sunscreen agents, including but not limited to gadusol, prasiolin, shinorine, *porphyra*-334, and mycosporine-glycine-alanine.

In addition to gadusporine A, gadusporine B, gadusporine C, or a combination thereof (in some examples further including one or more of gadusol, prasiolin, shinorine, *porphyra*-334, and mycosporine-glycine-alanine) sunscreen compositions of the present disclosure can in some examples further include polymers and copolymers capable of forming a film. Useful film forming polymers can either be synthetic or naturally derived. For example, film forming polymers may include water dispersible polymers, either naturally or synthetically derived. The film forming polymers (e.g., film forming agents) may in some examples comprise waterproofing agents.

Examples of film-forming/waterproofing agents can include but are not limited to polyethylene, tricontanyl PVP, acrylates/acrylamide copolymer, butylated PVP, acrylates/C12_22 alkylmethacrylate copolymer, octadecene/MA copolymer, *Brassica Campestris/Aleuritis* Fordi Oil copolymer, wax, acrylates copolymer, PVP/eicosene copolymer, PVP/hexadecene copolymer, decamethyl cyclopentasiloxane, VP/dimethiconylacrylate/polycarbamyl polyglycol ester, trimethylsiloxysilicate and any combinations thereof.

In addition to gadusporine A, gadusporine B, gadusporine C, non-limiting examples of suitable additional sunscreen components that can be used in the disclosed compositions include clays, agars, guars, nanoparticles, native and modified starches, modified cellulosics, zinc oxide, and titanium dioxide and any combination of the foregoing. Modified starches include, for example, DRY-FLO® PC lubricant (aluminum starch octenylsuccinate), DRY-FLO® AF lubricant (corn starch modified), DRY-FLO® ELITE LL lubricant (aluminum starch octenylsuccinate (and) lauryl lysine), DRY-FLO® ELITE BN lubricant (aluminum starch octenylsuccinate (and) boron nitride), all commercially available from National Starch and Chemical Company (Bridgewater, NJ).

Sunscreen compositions can optionally further include additional active agents. Suitable active agents include, for example, anti-acne agents, antimicrobial agents, anti-inflammatory agents, analgesics, anti-erythemal agents, antiruritic agents, antiedermal agents, antipsoriatic agents, antifungal agents, skin protectants, vitamins, antioxidants, scavengers, antiirritants, antibacterial agents, antiviral agents, antiaging agents, protoprotection agents, hair growth enhancers, hair growth inhibitors, hair removal agents, anti-dandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, hydroxyalkyl urea, amino acids, peptides, minerals, ceramides, biohyaluronic acids, vitamins, skin lightening agents, self-tanning agents, coenzyme Q10, niacinimide, capsaicin, caffeine, and any combination of any of the foregoing.

Sunscreen compositions can optionally include one or more aesthetic enhancers (i.e., a material that imparts desirable tactile, visual, taste and/or olfactory properties to the surface to which the composition is applied) and can be either hydrophilic or hydrophobic.

Sunscreen compositions can optionally include one or more adjuvants, such as pH adjusters, emollients, humectants, conditioning agents, moisturizers, chelating agents, propellants, rheology modifiers and emulsifiers such as gelling agents, colorants, fragrances, odor masking agents, UV stabilizer, preservatives, and any combination of any of the foregoing. Examples of pH adjusters include, but are not limited to, aminomethyl propanol, aminomethylpropane diol, triethanolamine, triethylamine, citric acid, sodium hydroxide, acetic acid, potassium hydroxide, lactic acid, and any combination thereof.

Rheology modifiers may include one or more of a polymeric emulsifier, natural gum, synthetic gum, anionic associative rheology modifier, nonionic associative rheology modifier, thickening agent, polysaccharide thickening agent, synthetic polymer, natural polymer, associative thickener, oil-thickening agent, polymeric emulsifier, stabilizer, and any combinations thereof.

Thickening agents relevant to the sunscreen compositions of the present disclosure can include but are not limited to synthetic gum, natural gum, anionic associative rheology modifier, nonionic associative rheology modifier, synthetic polymer, natural polymer, polysaccharide thickening agent, acrylates/C10-30 alkylacrylate crosspolymer, associative thickener, acrylates/beheneth-25 methacrylate copolymer, PVP, PEG-150/decyl alcohol/SMDI copolymer, acrylates copolymer, acrylates/steareth-20 methacrylate copolymer, oil-thickening agent, PVM/MA decadiene crosspolymer, PEG crosspolymer, acrylates/palmeth-25 acrylates copolymer, acrylates/aminoacrylates/C10-30 alkyl PEG-20 itaconate copolymer, carbomer, sodium polyacryloyldimethyl taurate, polyether-1, sodium magnesium silicate, sodium polymethacrylate, sodium acryloyldimethyl taurate copolymer, sodium carragenan, bentonites, trihydroxystearin, sodium polyacrylate, polysaccharide, sodium carboxymethyl dextran, sodium carbomer, hydroxyethylcellulose, hydroxypropyl cyclodextran, polyacrylate, aluminum-magnesium hydroxide stearate, xanthan gum, and any combinations thereof.

Suitable conditioning agents include, but are not limited to, cyclomethicone; petrolatum; dimethicone; dimethiconol; cocoglyceride; silicone, such as cyclopentasiloxane and diisostearoyl trimethylolpropane siloxy silicate; sodium hyaluronate; isostearyl linoleate; alkanes; coconut oil; isopropyl palmitate; jojoba oil; dicapryl maleate; fatty alcohol; hexadecyl alcohol; benzoic acid esters of alcohols; soybean oil; cetyl alcohol; linoleic acid; PPG-12/saturated methylene diphenyldiisocyanate copolymer; polyoxypropylene butyl ether; caprylic/capric triglyceride; aloe extracts; cocoa butter; urea; polyoxypropylene cetyl ether; amodimethicone; trideceth-12; castor oil; diisopropyl adipate; stearic acid; cekimonium chloride; olive oil; octyl stearate; hydroxybenzoate esters; fatty acid; mineral oil; isopropyl myristate; oleic acid; C12-C15 alkyl benzoate; diphenyl dimethicone; isononyl iso-nonanoate; propylene glycol; ether; lanolin oil; dimethyl polysiloxane; avocado oil; glycerin; hydroxyalkyl urea; tocopherol; quaternary amines; and any combination thereof.

Suitable preservatives include, but are not limited to, chlorophenesin, sorbic acid, disodium ethylenedinitrilotetraacetate, vitamin C, butylated hydroxytoluene, phenoxyethanol, butylparaben, diazolidinyl urea, methylparaben, iodopropynyl butylcarbamate, chloromethylisotiazolinone, ethylparaben, propylparaben, isobutylparaben, phytic acid, vitamin E and its derivatives, benzyl alcohol, imidazolidinyl urea, vitamin E acetate, sodium dehydroacetate, methylchloroisothiazolinone, methylisothiazolinone, and any combination thereof.

Suitable humectants include, but are not limited to, propylene glycol, pentylene glycol, hexylene glycol, butylene glycol, propylene glycol, aloe vera gel, alpha hydroxy acids such as lactic acid, egg yolk and egg white, sorbitol, glyceryl triacetate, honey, lithium chloride, PEG-4, salicylic acid, glycerin, hyaluronic acid, urea, panthenol, sodium lactate, glycol, and any combination thereof.

In some examples, sunscreen compositions of the present disclosure can include one or more sun protection factor (SPF) boosters. Examples include but are not limited to styrene/acrylates copolymer, sodium bentonite, highly purified white sodium bentonite, montmorillonite, hydrogel, and any combinations thereof.

Generally, sunscreen compositions of the present disclosure contain at least one or more sunscreen actives or agents, such as gadusporine A, gadusporine B, gadusporine C, or a combination thereof, in an amount of about 0.25 to about 30% by weight, based on total weight of the compositions; one or more film forming polymers in an amount of about 0.05 to about 10% by weight, based on total weight of the composition; and heat treated xanthan gum in an amount of about 0.05 to about 20% by weight, based on total weight of the composition, with the remaining composition including other ingredients according to the desired end formulation.

In some embodiments, other sunscreen agents may be included, for example in addition to one or more of gadusporine A, gadusporine B, gadusporine C, and gadusol. Such agents may include but are not limited to zinc oxide, benzophenone-1, benzophenone-2, benzophenone-3, benzophenone-4, benzophenone-6, benzophenone-8, benzophenone-12, para-aminobenzoic acid (PABA), ethyl dihydroxypropyl-PABA, octyl dimethyl PABA, glyceryl PABA, butyl methoxydibenzoylmethane, bis-ethylhexyloxyphenol methoxyphenyl triazine, methoxycinnamate, 2-phenylbenzimidazole-5-sulphonic acid, 3-(4-methyl benzyldine)boran-2-one(methyl benzylidinecamphor), triethanolamine salicylate, octyl methoxycinnamate, methyl anthranilate, octyl triazone, octyl salicylate, homosalate, octocrylene, 3-(4-methylbenzylidene)-camphor, benzotriazole, phenylbenzimidazole-5-sulfonic acid, methylene bis-benzotrizolyl tetramethylbutyl phenol, red petrolatum, titanium dioxide, and any combinations thereof.

In some examples, the one or more sunscreen agents may be present in an amount to achieve a SPF between about 2 to about 60.

Deposit of Biological Material

The following biological material has been deposited under the terms of the Budapest Treaty with The American Type Culture Collection, and given the following accession number:

| Deposit | Accession Number | Date of Deposit |
| --- | --- | --- |
| *Streptomyces coelicolor*/pTMAO-G3 | PTA-126147 | Aug. 30, 2019 |

The following non-liming examples are provided to illustrate certain particular features and/or embodiments. These examples should not be construed to limit the disclosure to the particular features or embodiments described.

EXAMPLES

Example 1

Design of a Synthetic Operon for Forming MAA Analogs

This Example demonstrates a synthetic operon capable of forming MAA analogs containing a gadusol core in a *Streptomyces* heterologous host.

Figure 3:
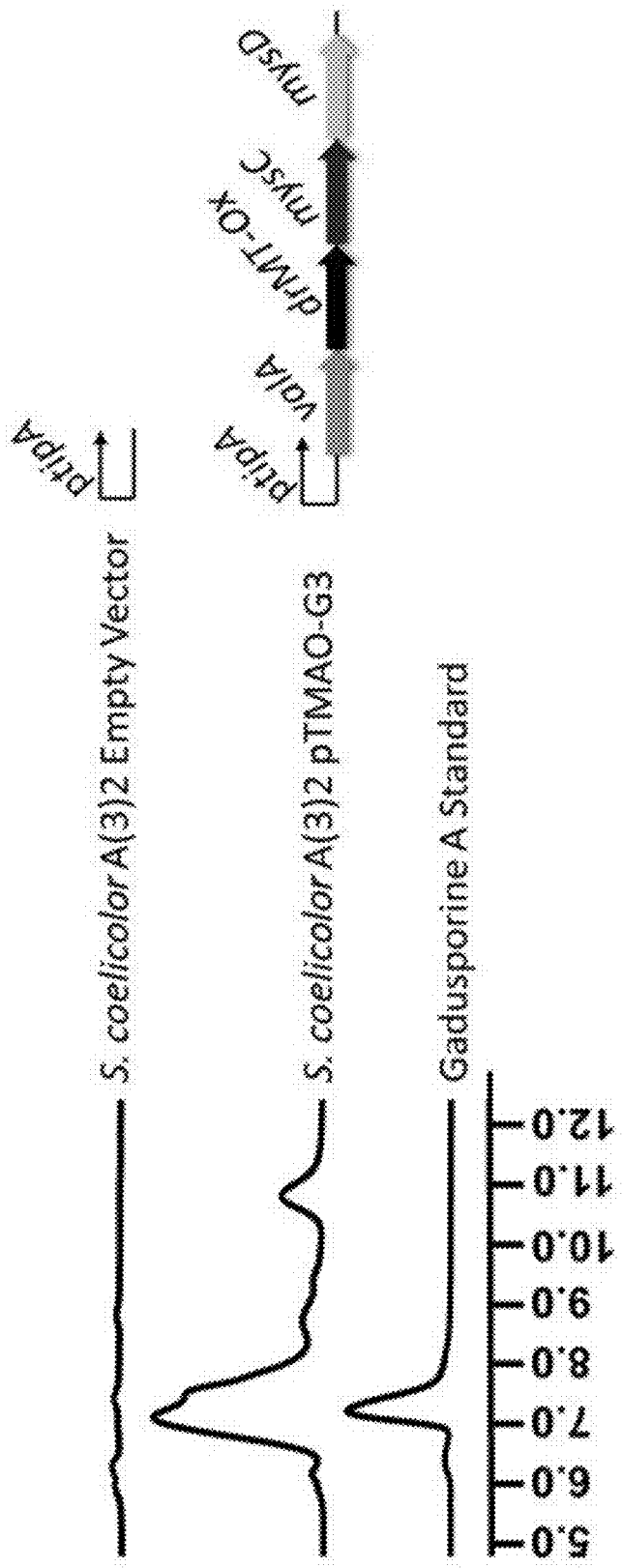
FIG. 3 depicts a high performance liquid chromatography (HPLC) chromatogram at 340 nm showing gadusporine production by *S. coelicolor* A(3)2 pTMAO-G3.

For this Example, the model EEVS gene valA from the validamycin pathway in *S. hygroscopicus* (refer to FIG. 2) was employed, as valA does not require optimization for heterologous expression in *Streptomyces*. The zebrafish MT-Ox gene was codon-optimized for expression in *S. coelicolor* (see sequence below). The *Rhodococcus fascians* D188 MAA genes mysC and mysD (see Table 2) were cloned after the above genes, forming plasmid pTMAO-G3 (FIG. 3). After conjugation into *S. coelicolor* A(3)2, *S. coelicolor* pTMAO-G3 was formed.

TABLE 2

The *Rhodocous fascians* D188 MAA operon

| Gene name | Locus | Function |
|---|---|---|
| mysA | a3L23_Rs04425 | Desmethyl-4-deoxygadusol synthase |
| mysB | a3L23_Rs04430 | O-methyltransferase |
| mysC | a3L23_Rs04435 | ATP-Grasp ligase-like |
| mysD | a3L23_Rs04440 | D-Ala D-Ala ligase-like |

Briefly, a *Streptomyces* codon-optimized drMT-Ox was ordered from Twist Bioscience (San Francisco, CA). valA and drMT-Ox were cloned into pXY201-eGFP (enhanced green fluorescent protein) by DNA assembly at the T7-gene leader peptide and eGFP start sites, forming pTMAO-G1. valA was amplified from a previously formed construct valA-pRSET-B. The ribosome binding sequence (RBS) from pXY201 was placed before drMT-Ox. To form plasmids pTMAO G2 and G3, the *R. fascians* D188 mysCD genes were amplified together from genomic DNA and inserted directly after drMT-Ox, with an RBS placed before mysC but relying on the native RBS for mysD, forming pTMAO-G3. Plasmids were sequenced by Sanger sequencing (Center for Genome Research and Biocomputing, Oregon State University, Corvallis, OR). All primers were designed using Benchling (San Francisco, CA). PCR was performed using PrimestarGXL (Takara, Kusatsu, Shiga, Japan), following the manufacturers rapid PCR protocol with 35 cycles, except for using 1 µL polymerase per 50 µL reaction instead of 2 µL and with 2% DMSO to amplify pXY201-eGFP for DNA assembly. All PCR products were purified by gel extraction. The New England Biolabs (NEB, Ipswich, MA) HiFi DNA assembly 2× master mix was used for DNA assembly, forming plasmid pTMAO-G3. Clones were identified using colony PCR using primers for mysC and the Onetaq quickload 2× mastermix (NEB, Ipswich, MA) using the manufacturers protocol with a TM of 60° C. and extension time of 1 minute and 35 cycles.

Example 2

Heterologous Expression of pTMAO-G3 in *S. coelicolor* A(3)2 pTMAO-G3 was transferred to *S. coelicolor* A(3)2 through intergeneric conjugation with *E. coli* ET12567 (pUZ8002) as the donor strain, forming *S. coelicolor* A(3)2 pTMAO-G3. *S. coelicolor* A(3)2 pTMAO-G3 was grown in 5 ml of R5A (Medium A: $K_2SO_4$: 0.25 g, $MgCl_2 \cdot 6H_2O$: 10.12 g, glucose: 10 g, Difco yeast extract: 5 g, Difco casamino acids: 0.1, Distilled water: 800 mL, TES buffer 5.73 g; Media B (Each component in a separate bottle, sterilized by autoclaving) Trace element solution: 2 mL, $KH_2PO_4$ (0.5%, w/v): 10 mL, $CaCl_2 \cdot 2H_2O$ (3.68%, w/v): 4 mL, L-proline (20%, w/v): 15 mL. Trace element solution (1 L): $ZnCl_2$: 40 mg, $FeCl_3 \cdot 6H_2O$: 200 mg, $CuCl_2 \cdot 2H_2O$: 10 mg, $MnCl_2 \cdot 4H_2O$: 10 mg, $Na_2B_4O_7 \cdot 10H_2O$: 10 mg, $(NH_4)_6Mo_7O_{24} \cdot 4H_2O$: 10 mg, 1M NaOH: 5 mL.) medium in culture tubes with two glass beads shaking at 30° C. for ~7 days. 1 mL of seed culture was added to 100 mL of R5 medium containing 50 µg/mL apramycin in 500 mL Erlenmeyer Shake Flasks with a spring in the bottom of the flask. After 24 hours, cultures were induced with a final concentration of 50 µg/ml thiostrepton, then allowed to grow for 13 more days.

Example 3

Purification and Structural Determination of Gadusporines

*S. coelicolor* A(3)2 pTMAO-G3 was cultured as described above at larger scales and 225 mL of *S. coelicolor* pTMAO-G3 culture broth was dried to ~20 mL and passed through a C18 solid phase extraction (SPE) column. Gadusol and gadusporines were mostly un-retained, however, washing with water for 1-2 column volumes (CVs) eluted the remaining compounds. The eluent was combined and dried to ~20 mL, which was applied directly to a 300 mL Bio-Rad AG®-1×8 (acetate form) column. After washing with 2 L of water, 500 mM acetic acid was used to elute gadusol and gadusporines. All fractions containing both gadusol and gadusporines were combined and fractions lacking gadusol but containing gadusporines were combined separately and dried. The gadusol-free fraction was further purified using the preparative HPLC as described previously to give gadusporine A (9.0 mg) (see FIG. 5A) as two different isomers. All NMR experiments were performed on a 700 MHz Bruker NMR Spectrometer with a cryo probe at the Oregon State University (OSU) NMR facility. The molar extinction coefficient of gadusporine A was determined by dissolving 0.6 mg in 50 mM phosphate buffer at pH 7.0 in a 25 mL volumetric flask then measuring UV absorbance at 340 nm.

Gadusporine A (see FIG. 5A), a yellow-brown solid, UV (50 mM phosphate buffer pH 7) $\lambda_{max}$ 340 nm, (50 mM acetic acid pH 3) $\lambda_{max}$ 338 nm. $^1$H NMR (700 MHz, $D_2O$) and $^{13}$C NMR (175 MHz, $D_2O$) see Table 3. HR-ESIMS m/z349.1239 [M+H]$^+$ (calculated for $C_{13}H_{20}N_2O_9$, 349.1247).

The gadusol-containing fraction was also purified using the preparative HPLC to give gadusporine B and gadusporine C (see FIG. 5A), however, some gadusol still co-eluted. Gadusporine B and gadusporine C were then separated from gadusol using a 5 µm Acentis-Si 10×250 mm semi-prep column in HILIC mode. Solvent A=5 mM ammonium acetate, pH 7.0; Solvent B=acetonitrile; Flow rate=2.0 mL/min; Gradient: 95% B for 5 min, 95%→60% B over 3 min, 60% B held for 10 min, 60%→95% B over 5 min, 95% B for 20 min for column equilibration. Fractions containing gadusporine B were combined, dried, and de-salted using Sephadex LH-20 to give pure gadusporine B (0.8 mg). Fractions containing gadusporine C were also combined, dried, and de-salted using Sephadex LH-20 to give pure gadusporine C (<0.1 mg). Separation was also achieved by replacing the 5 mM ammonium acetate with 0.1% acetic acid, removing the need for de-salting for future purifications.

Gadusporine B (see FIG. 5A), a yellow-brown solid, UV (50 mM phosphate buffer pH 7) $\lambda_{max}$ 340 nm, (50 mM acetic acid pH 3) $\lambda_{max}$ 338 nm. $^1$H NMR (700 MHz, D$_2$O) and $^{13}$C NMR (175 MHz, D$_2$O) see Table 3 below. HR-ESIMS m/z333.1289 [M+H]+(calculated for $C_{13}H_{20}N_2O_8$, 332.1219).

Gadusporine C (see FIG. 5A) was only identified by HR-ESIMS. HR-ESIMS m/z 363.1380 [M+H]$^+$ (calculated for $C_{14}H_{22}N_2O_9$, 362.1325).

In more detail, gadusol was initially identified by HPLC of *S. coelicolor* pTMAO-G3 culture broth at yields of 520 mg/L. HPLC also revealed the production of two new mycosporine analogs, gadusporines A and B. Both analogs had a UV maximum at 338 nm under acidic conditions with retention times (x-axis, in minutes) at 7.1 and 9.9 minutes respectively (FIG. 3). Gadusporine A was produced at 20 mg/L. Gadusol was produced by pTMAO-G1 at of 29 mg/L.

Figure 6A:
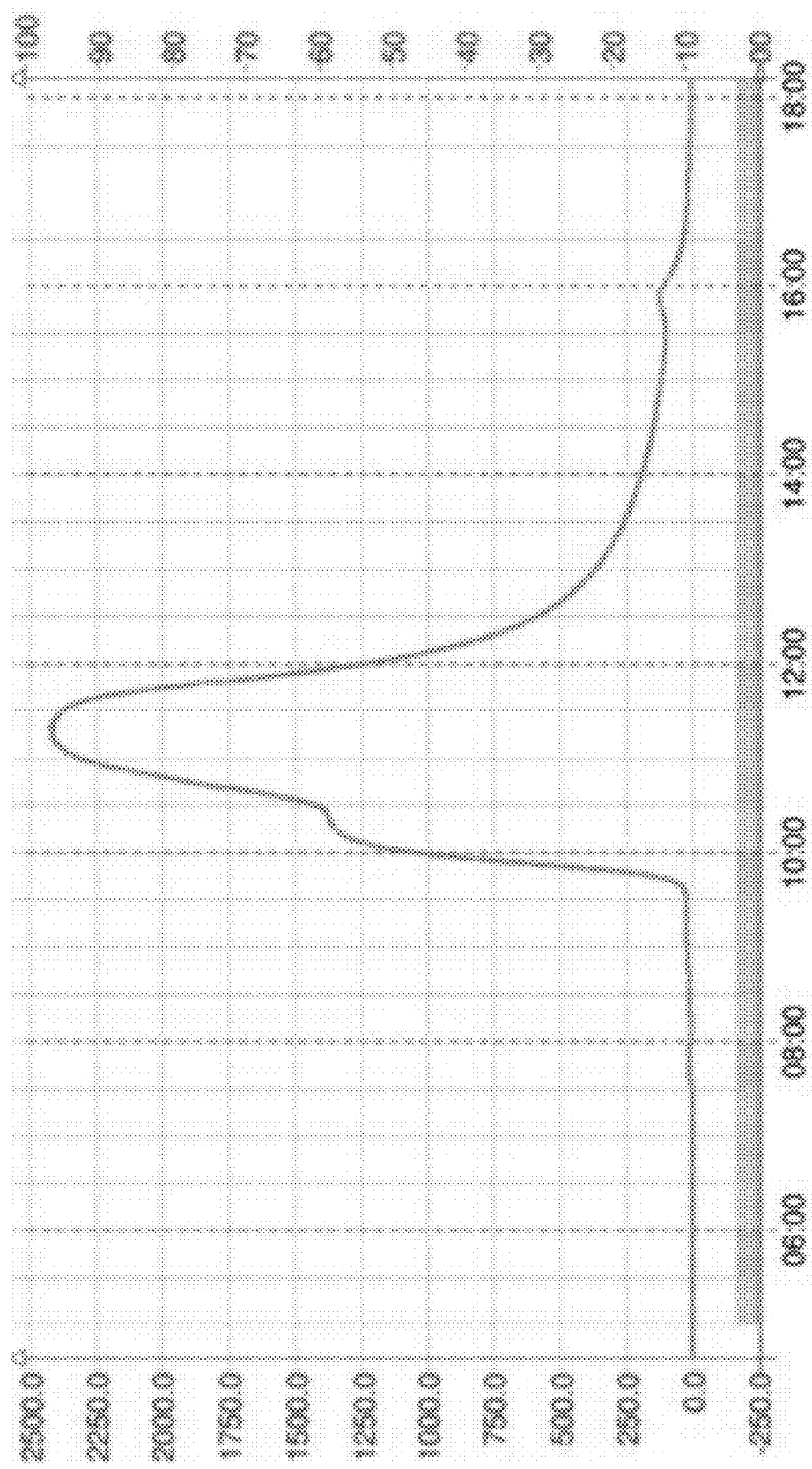
FIGS. 6A and 6B illustrate purification of gadusporines.
Figure 6B:
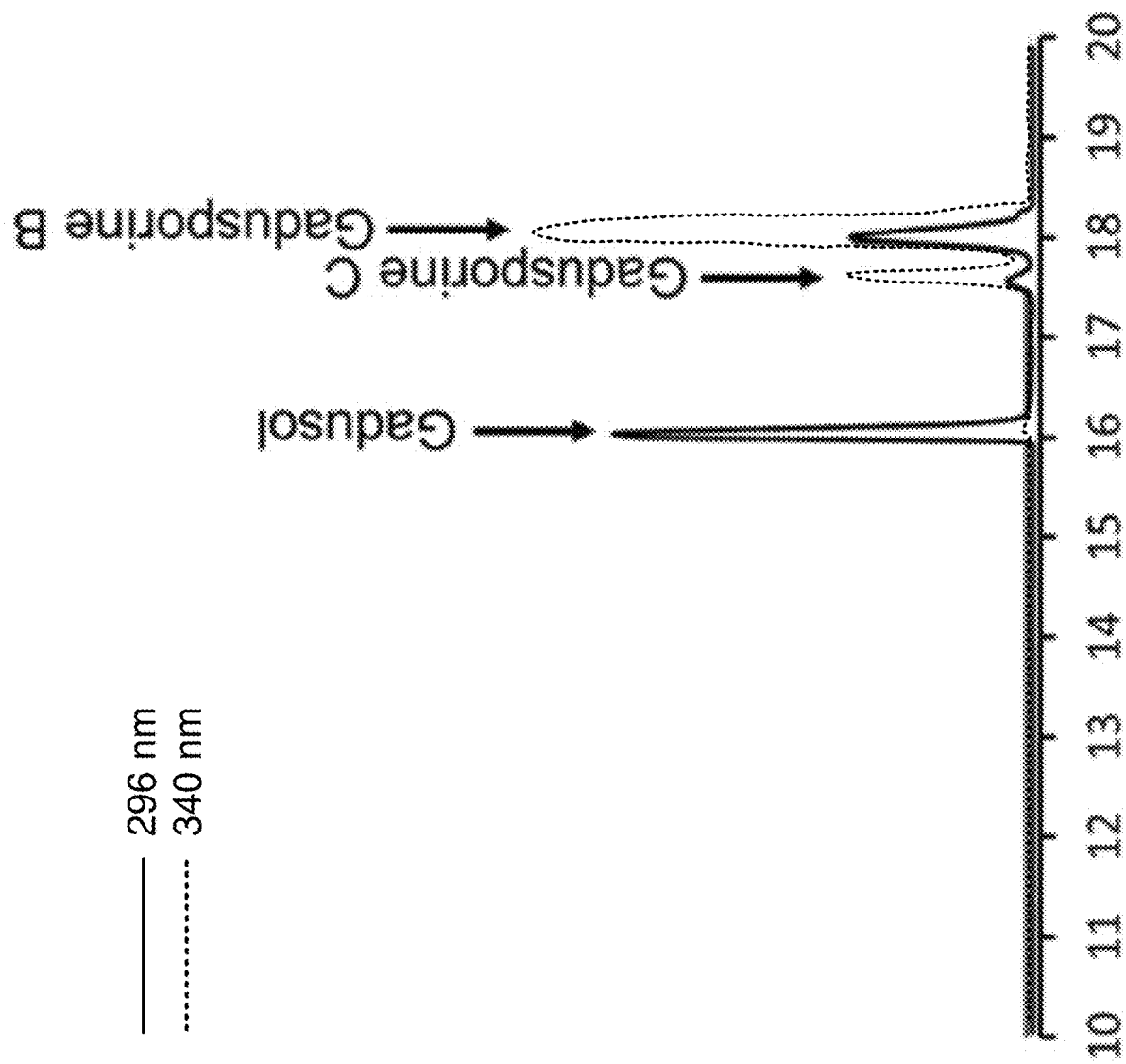

To purify gadusporines, the culture broth was dried and passed through a C18 SPE cartridge, then applied to a Bio-Rad (Hercules, CA) AG 1-×8 anion exchange column (300 mL resin in total) in acetate form. After washing with 7 column volumes deionized (DI) water, gadusol and gadusporines were eluted with 500 mM acetic acid. For the most part, gadusol and gadusporines co-eluted together, however, some gadusporines were retained longer than gadusol. These fractions lacking gadusol were combined and dried. The gadusol-containing and gadusol-free fractions were separately further purified by preparative C18 HPLC where gadusporine A was purified (FIG. 6A, gadusporine A shown only) and gadusporine B needed further separation from gadusol (not shown). Fractions containing all three compounds were further separated by hydrophilic interaction liquid chromatography (HILIC) (FIG. 6B).

Figure 4:
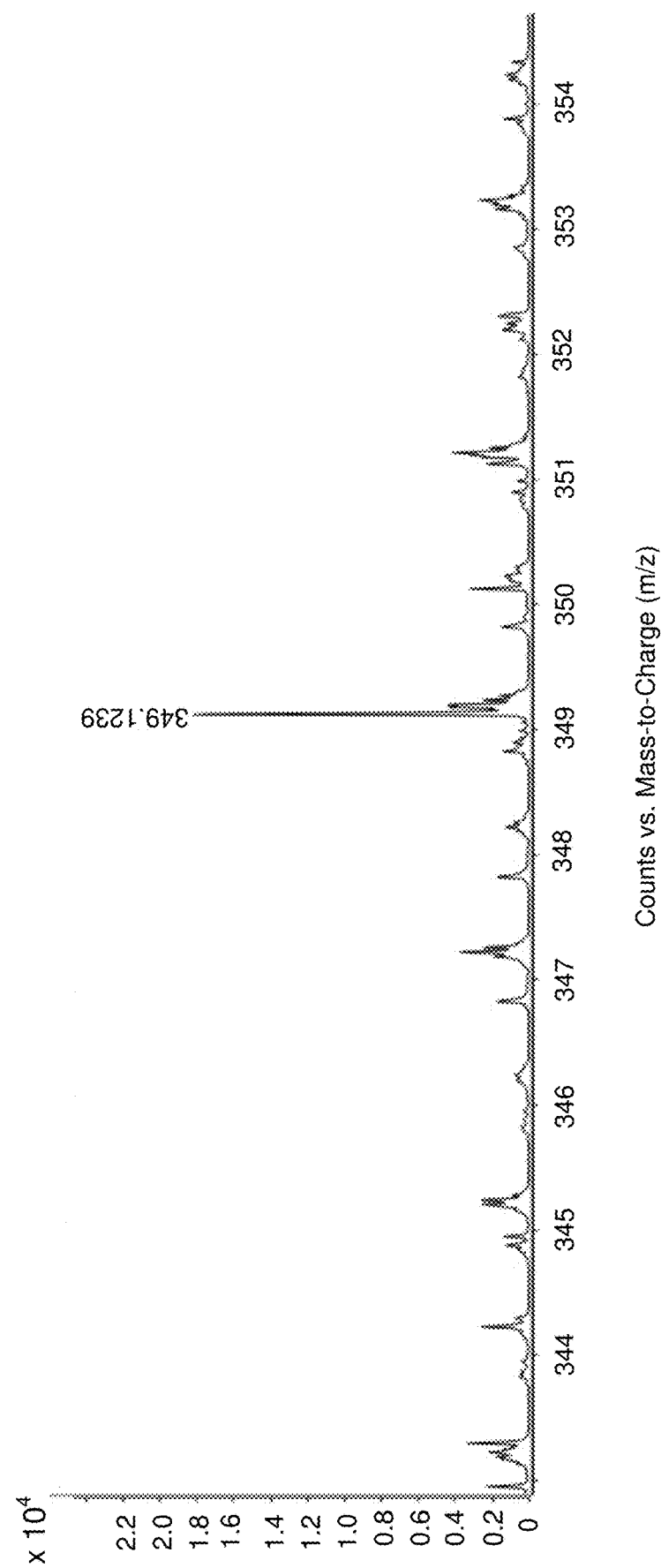
FIG. 4 depicts a high resolution-mass spectrometry (HR-MS) spectrum of gadusporine A.
Figure 5B:
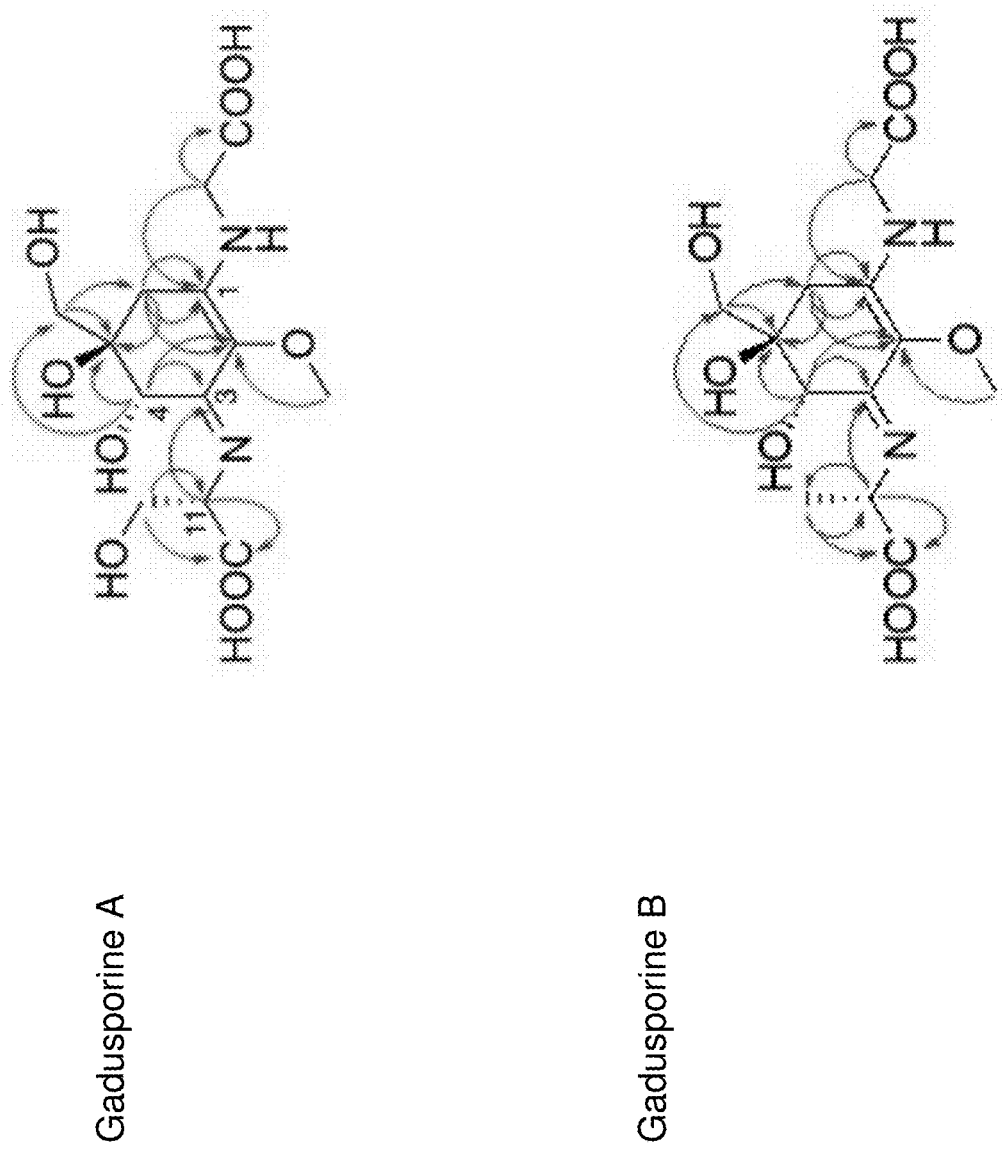
Figure 5C:
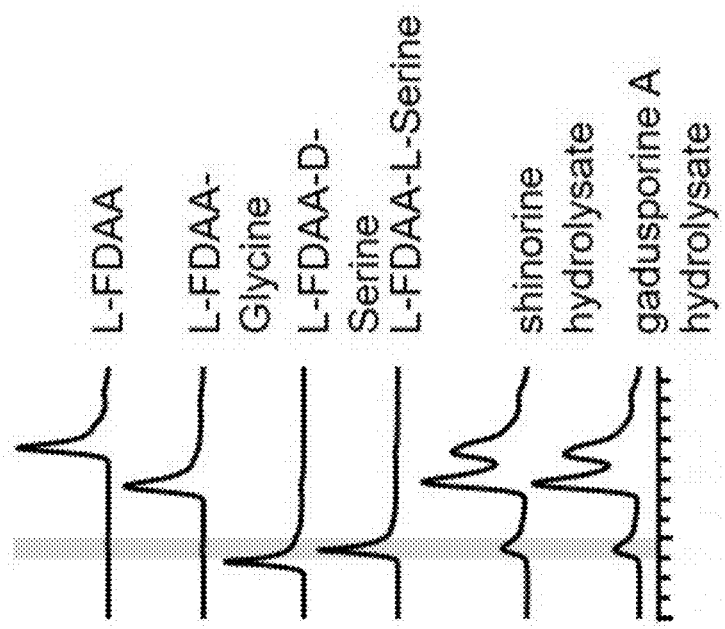
Figure 7:
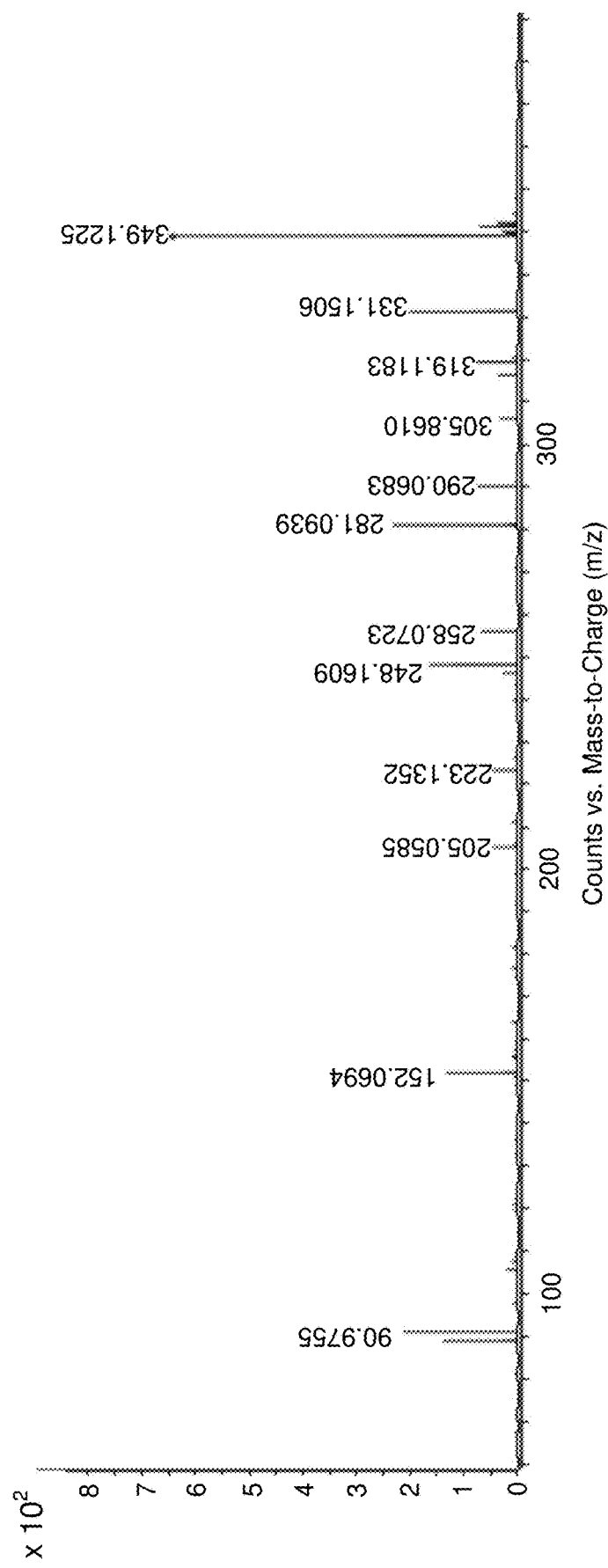
FIG. 7 depicts HR-MS fragmentation of gadusporine A.
Figure 11:
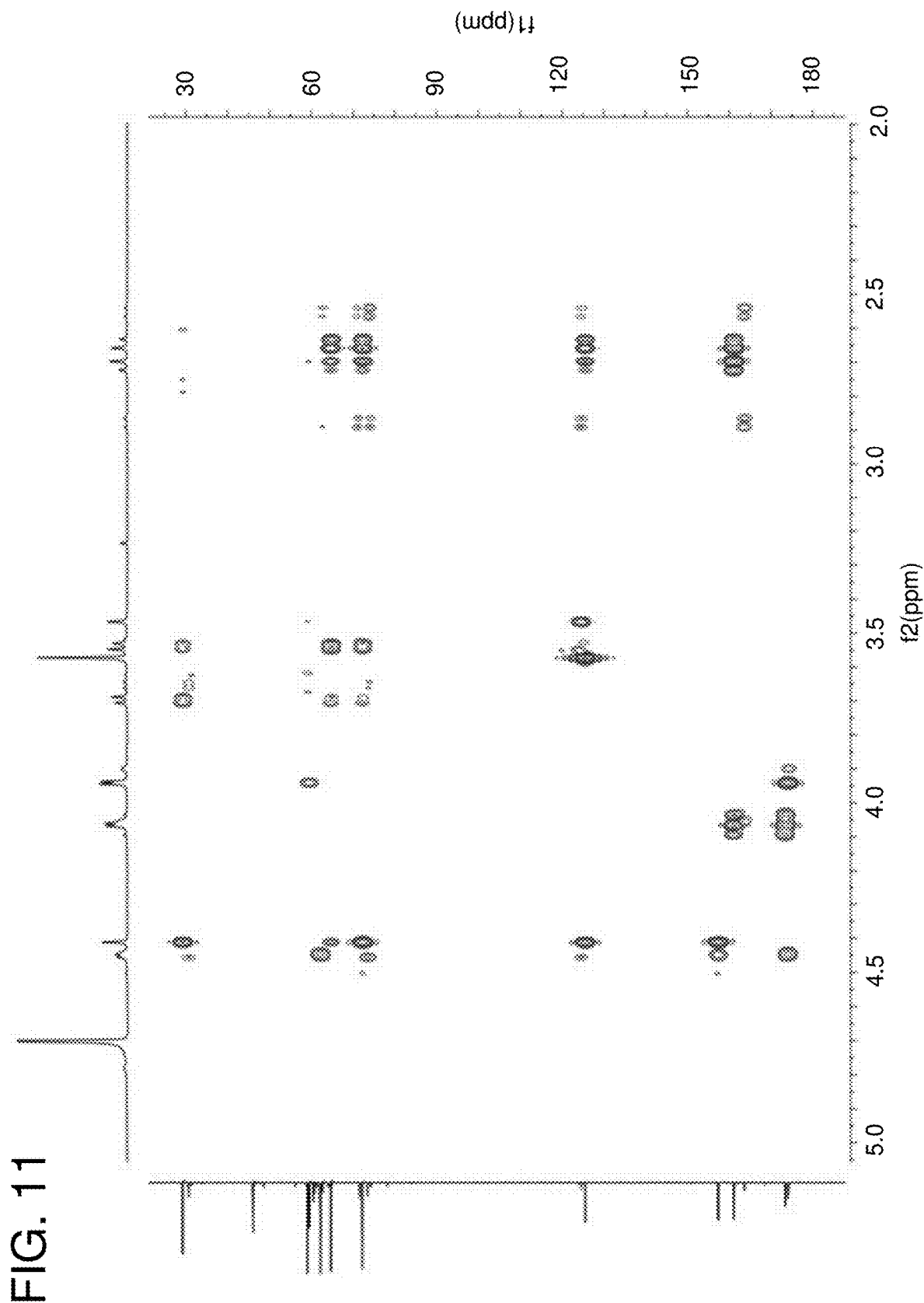
FIG. 11 depicts HMBC spectrum of gadusporine A.

Gadusporine A was purified as a yellow-brown solid. Gadusporine A had a predicted chemical formula of $C_{13}H_{20}N_2O_9$ (calculated m/z 349.1247 ([M+H]$^+$) and HR-MS detected an ion of m/z 349.1225 ([M+H]$^+$), −6.3 ppm below the calculated m/z (FIG. 4, FIG. 7). This suggested that gadusporine A was a hydroxylated shinorine analog. The full chemical structure of gadusporine A was elucidated by 1 D and 2D NMR (Table 3, FIGS. 8-11). 13 protons were identified by $^1$H NMR, where H-4 [4.41 (s)], H$_2$-6 [2.71 (d, J=18 Hz) and 2.64 (d, J=18 Hz)], H$_2$-7 [3.69 (d, J=12 Hz) and 3.53 (d, J=12 Hz)], and H$_3$-8 [3.57 (s)] resembled the same protons previously reported for gadusol. The H-6 resonance integrated as 2H, consistent with the expectation that H-6 was the ring methylene protons. The H-4 resonance integrated as 1H, therefore the hydroxyl group was attached to C-4. This also contrasts with H-4 from shinorine, where H-4 is not as far downfield and integrates as 2H. Different from gadusol were the proton resonances for H-9, H-11, and H-13, presumably representing the amino acid side chain moieties serine and glycine protons. The key HMBC correlations showed that H-11 (CH) and H-13 (CH$_2$) are adjacent to each other and that both H-11 and H-4 correlate to C-3 (FIG. 5B, FIG. 11). Therefore, the putative serine was located near the hydroxyl group. Marfey's analysis was used to confirm the identity of the amino acids and the absolute configuration of gadusporine A. Gadusporine A was hydrolyzed by 6N HCl and the hydrolysate was derivatized by L-FDAA (1-fluoro-2-4-dinitrophenyl-5-L-alanine amide), then compared to standards by HPLC. This demonstrated that L-serine and glycine were attached to the gadusol core (FIG. 5C).

TABLE 3

NMR spectroscopic data for gadusporine A and gadusporine B

| | gadusporine A | | gadusporine B | |
| --- | --- | --- | --- | --- |
| Position | $\delta_C$ | $\delta_H$ | $\delta_C$ | $\delta_H$ |
| 1 | 157.4 | — | 156.6 | — |
| 2 | 125.5 | — | 125.0 | — |
| 3 | 161.1 | — | 160.2 | — |
| 4 | 64.7 | 4.41 (s, 1H) | 64.8 | 4.40 (s, 1H) |
| 5 | 72.3 | — | 72.3 | — |
| 6 | 29.3 | 2.71 (d, J = 18 Hz, 1H), 2.64 (d, J = 18 Hz, 1H) | 29.2 | 2.68 (d, J = 18 Hz, 1H), 2.61 (d, J = 18 Hz, 1H) |
| 7 | 64.7 | 3.69 (d, J = 12 Hz, 1H), 3.53 (d, J = 12 Hz, 1H) | 64.7 | 3.69 (d, J = 12 Hz, 1H), 3.53 (d, J = 12 Hz, 1H) |
| 8 | 59.0 | 3.57 (s, 3H) | 58.9 | 3.55 (s, 3H), |
| 9 | 46.1 | 4.06 (dd, J = 5.5, 2 Hz, 2H) | 46.7 | 3.96 (d, J = 5.5 Hz, 2H) |
| 10 | 173.4 | — | 174.4 | — |
| 11 | 59.5 | 4.45 (m, 1H) | 54.2 | 4.29 (d, J = 7 Hz, 1H) |
| 12 | 174.0 | | 178.5 | |
| 13 | 62.1 | 3.94 (d, J = 5 Hz, 2H) | 18.5 | 1.44 (d, J = 7 Hz, 3H) |

Figure 8:
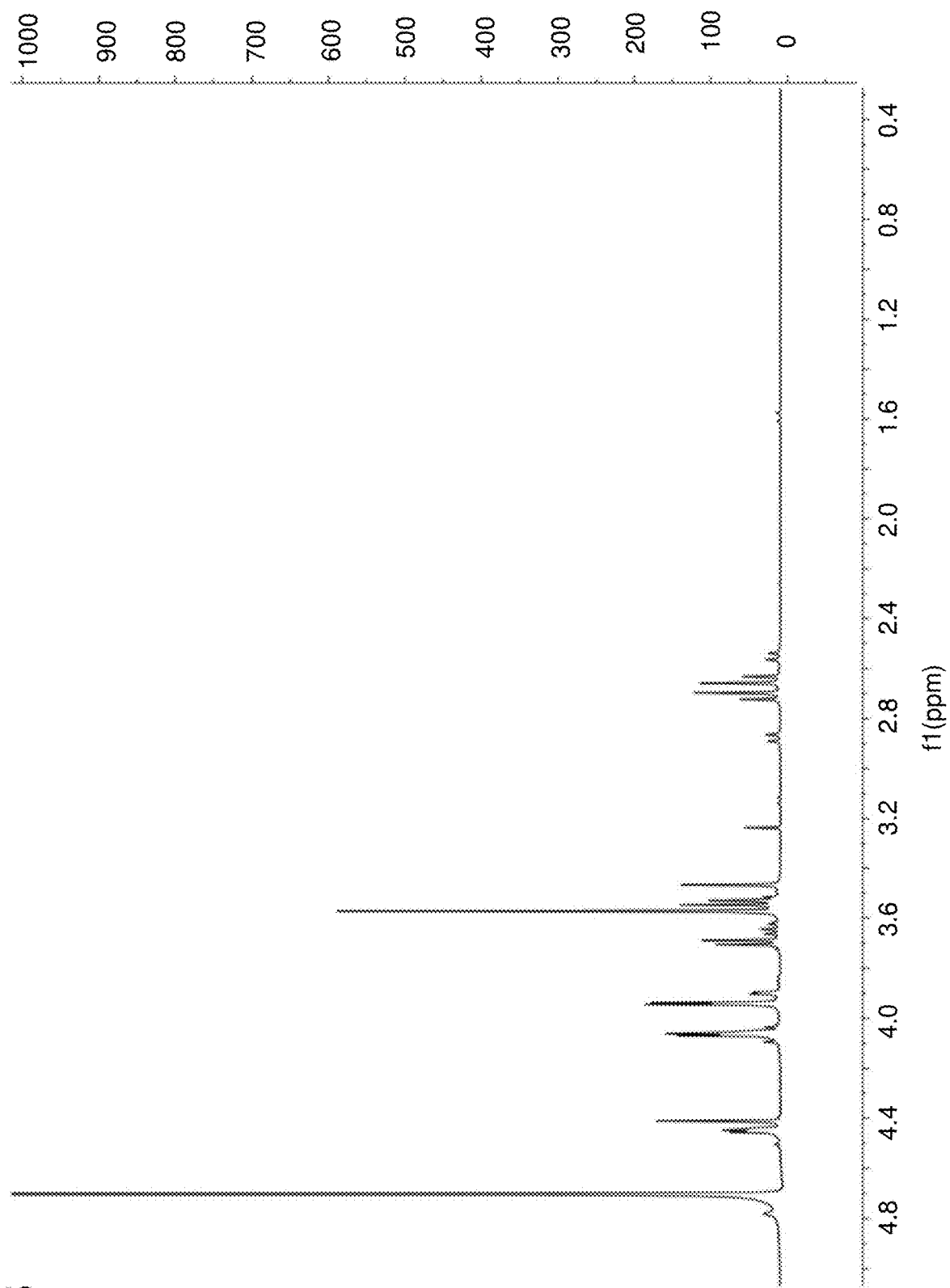
FIG. 8 depicts $^1$H NMR spectrum of purified gadusporine A. $^1$H NMR (700 MHz, D$_2$O) δ 4.45 (m, 1H), 4.41 (s, 1H), 4.06 (dd, J=5.5, 2 Hz, 2H), 3.94 (d, J=5 Hz, 2H), 3.69 (d, J=12 Hz, 1H), 3.57 (s, 3H), 3.53 (d, J=12 Hz, 1H), 2.71 (d, J=18 Hz, 1H), 2.64 (d, J=18 Hz, 1H)
Figure 9:
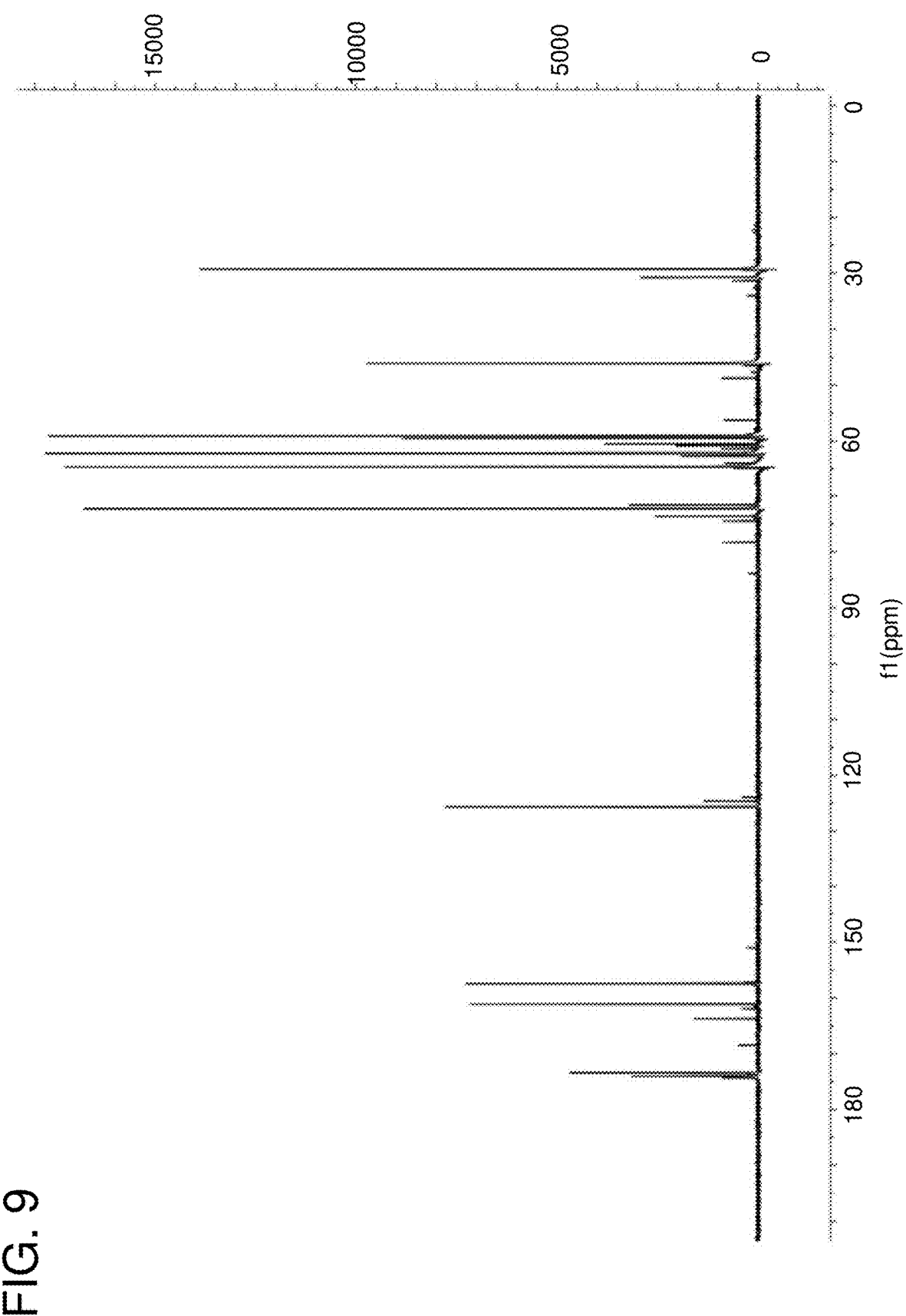
FIG. 9 depicts $^{13}$C NMR spectrum of purified gadusporine A. $^{13}$C NMR (176 MHz, D$_2$O) δ 174.00, 173.39, 161.12, 157.43, 125.58, 72.34, 64.71, 64.66, 62.16, 59.52, 59.08, 46.14, 29.32.
Figure 10:
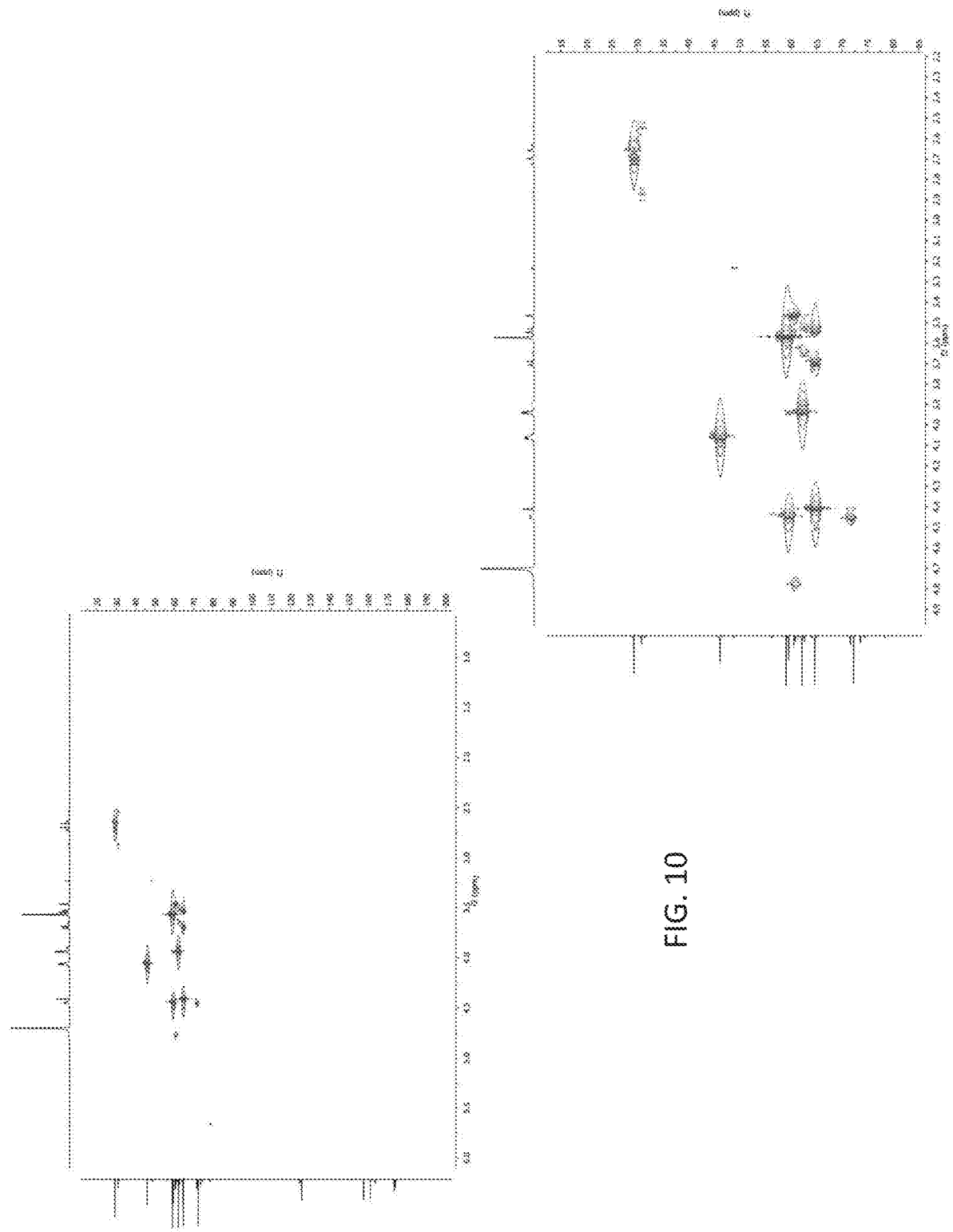
FIG. 10 depicts heteronuclear single quantum coherence (HSQC) spectrum of gadusporine A.
Figure 12:
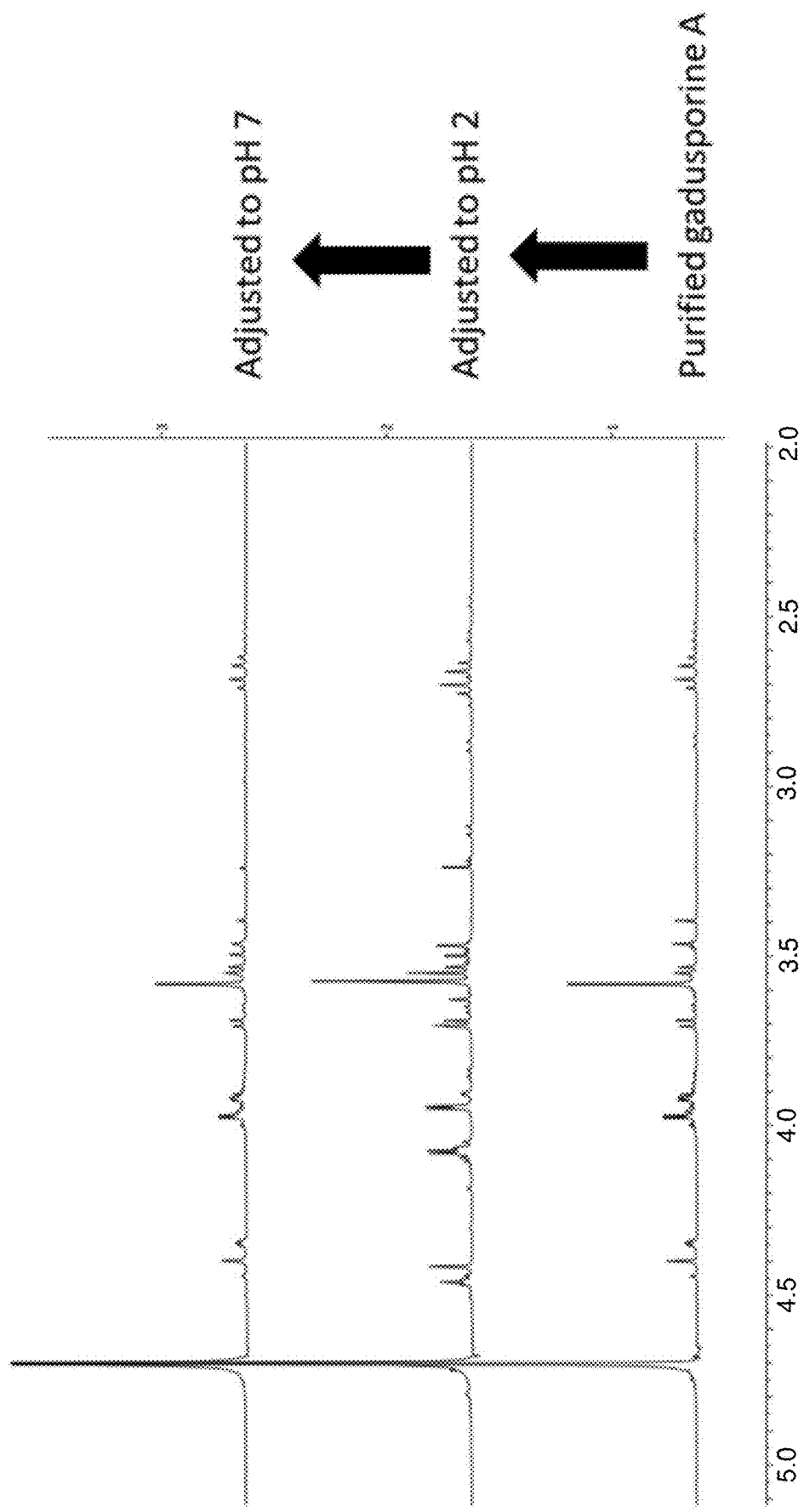
FIG. 12 depicts pH-dependent interconversion of gadusporine A isomers as observed by $^1$H NMR spectra.
Figure 19:
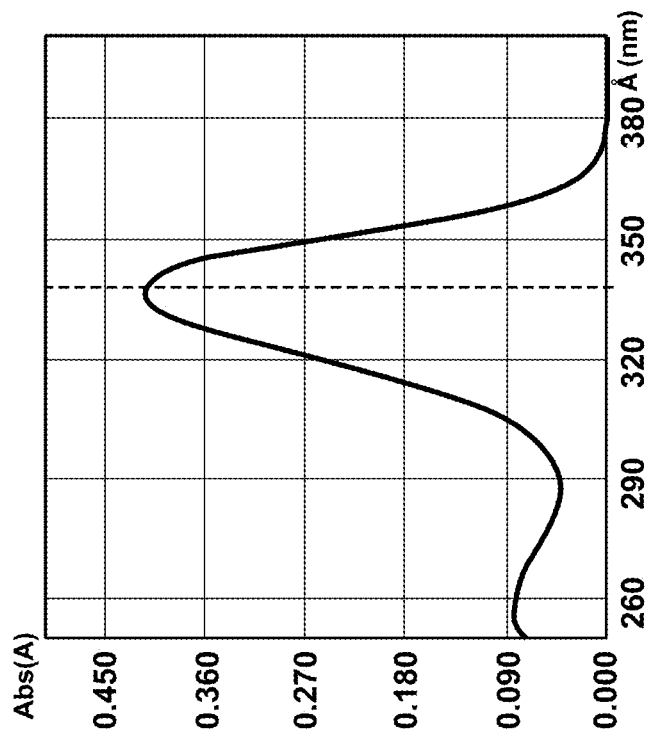
FIG. 19 depicts ultraviolet (UV) absorbance of gadusporine A at different pH values.
Figure 19:
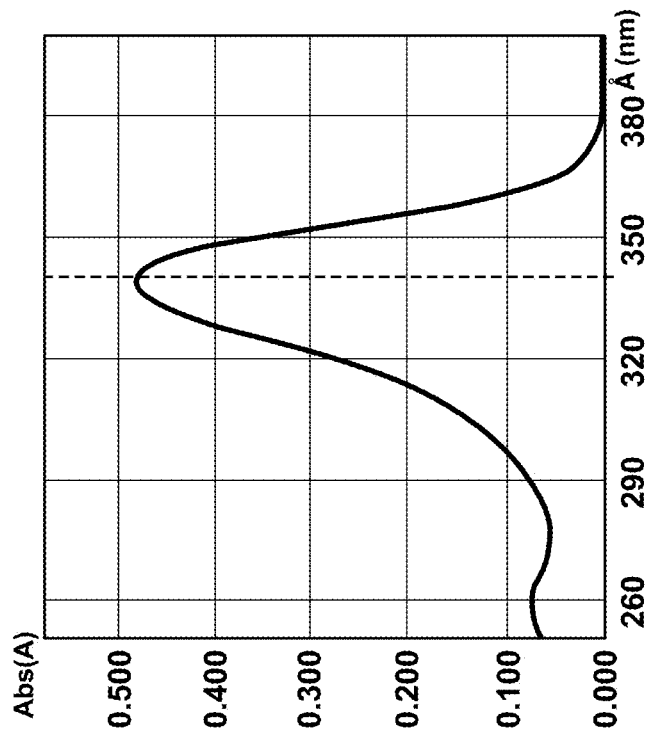

Gadusporine A was purified as two tautomers that are interconvertible, observed by changing the pH of gadusporine A solutions before $^1$H NMR experiments (FIG. 12). This is most easily observed by the change in chemical shift of the serine methine group, that starts as the most downfield proton but moves upfield at neutral pH and can be converted back (FIG. 12) and is also observed for the remaining protons on glycine and serine. This observation has been reported for porphyra-334 (see FIG. 1B) as well, where altering the pH changed $^1$H ppm values. The likely cause for both cases is differences in the conformation, hydrogen bonding, and resonance structures. FIG. 19 depicts ultraviolet (UV) absorbance of gadusporine A at different pH values. Another tautomer also exists in solutions of gadusporine A. The —OMe and ring methylene protons have extra signals that integrate to ~⅓ of the major signals, thus a 3:1 ratio of isomers (FIG. 8). However, most of the other isomer peaks largely overlap in the $^1$H NMR spectrum, making them hard to distinguish while the $^{13}$C peaks are more visible. For example, minor isomer H-6 overlaps with H-11 under acidic conditions but is easily observed at neutral conditions.

Despite the only difference being a hydroxy group, there a few notable differences between shinorine and gadusporine A. Shinorine is readily dissolved in methanol, whereas gadusporines have limited solubility. Shinorine has been reported to have $\lambda_{max}$=330 nm at pH 1.7 and $\lambda_{max}$=334 nm at pH 7. Gadusporine A shows $\lambda_{max}$=338 at pH 2.0 and $\lambda_{max}$=340 nm at pH 7.0, thus showing a narrower range of UV absorbance across pH values. Gadusporine A has a molar extinction coefficient ε=49,400, as measured in 50 mM phosphate buffer at pH 7.0, which is slightly higher than shinorine (ε=44,000), thus stronger UV absorbance activity.

Figure 13:
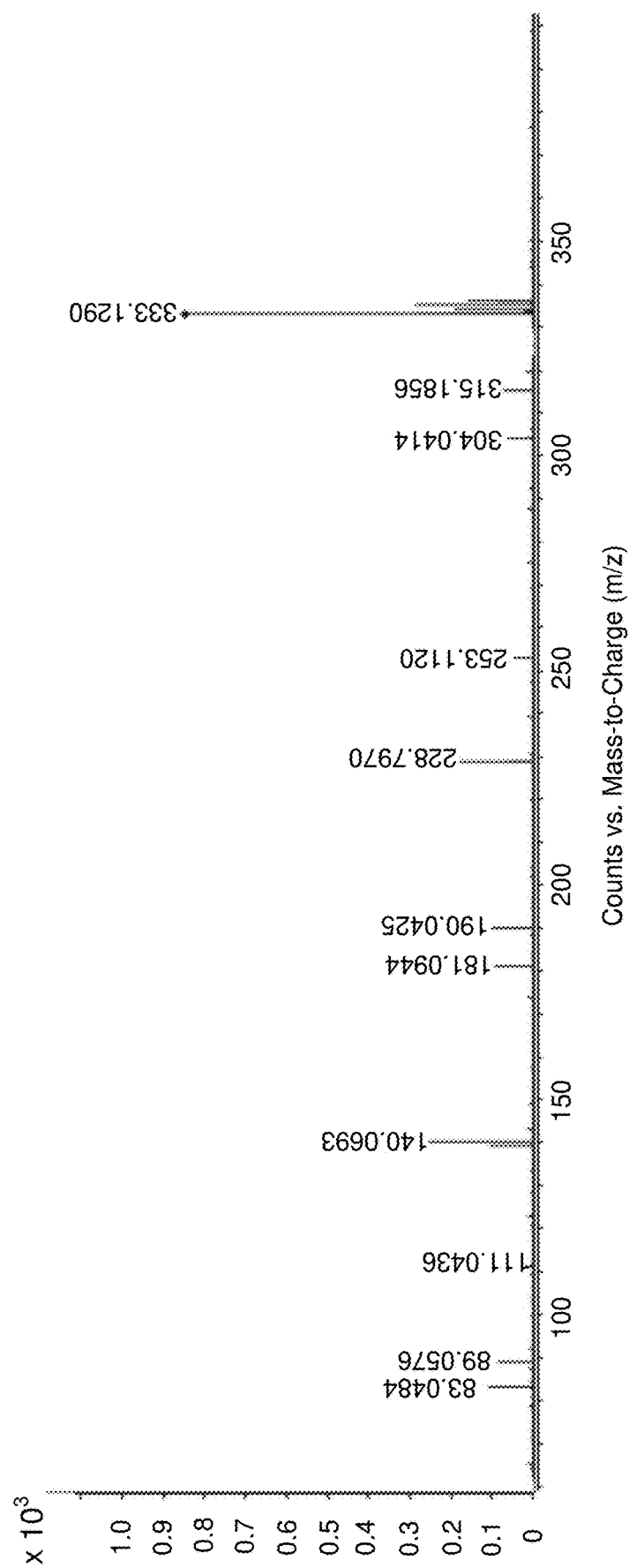
FIG. 13 depicts HR-MS fragmentation of gadusporine B.
Figure 14:
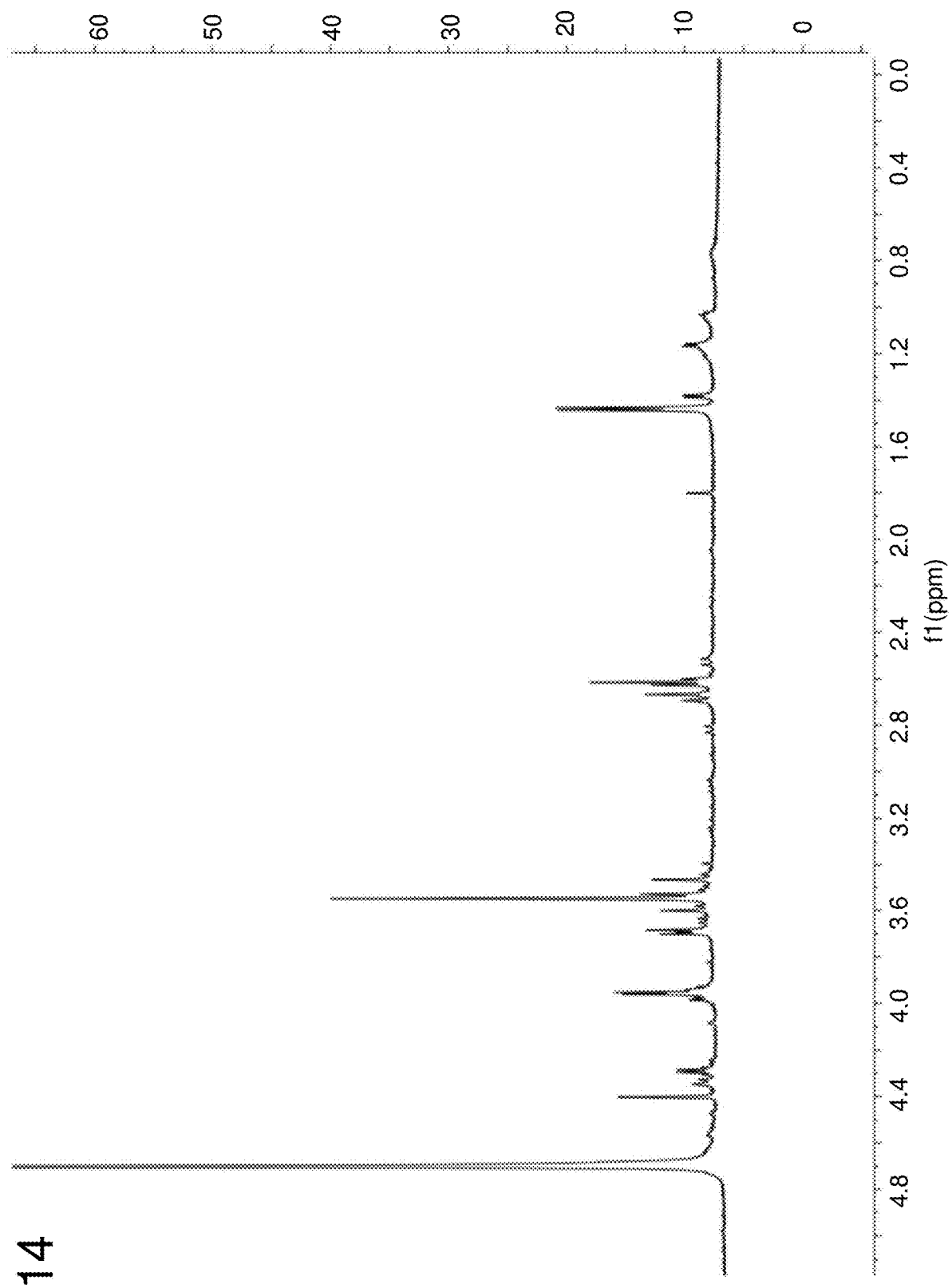
FIG. 14 depicts $^1$H NMR spectrum of gadusporine B; $^1$H NMR (700 MHz, D$_2$O) δ 4.40 (s, 1H), 4.29 (d, J=7 Hz, 1H), 3.96 (d, J=5.5 Hz, 2H), 3.69 (d, J=12 Hz, 1H), 3.53 (d, J=12 Hz, 1H) 3.55 (S, 3H), 2.68 (d, J=18 Hz, 1H), 2.61 (d, J=18, 1H), 1.44 (d, J=7.0 Hz, 3H)
Figure 15:
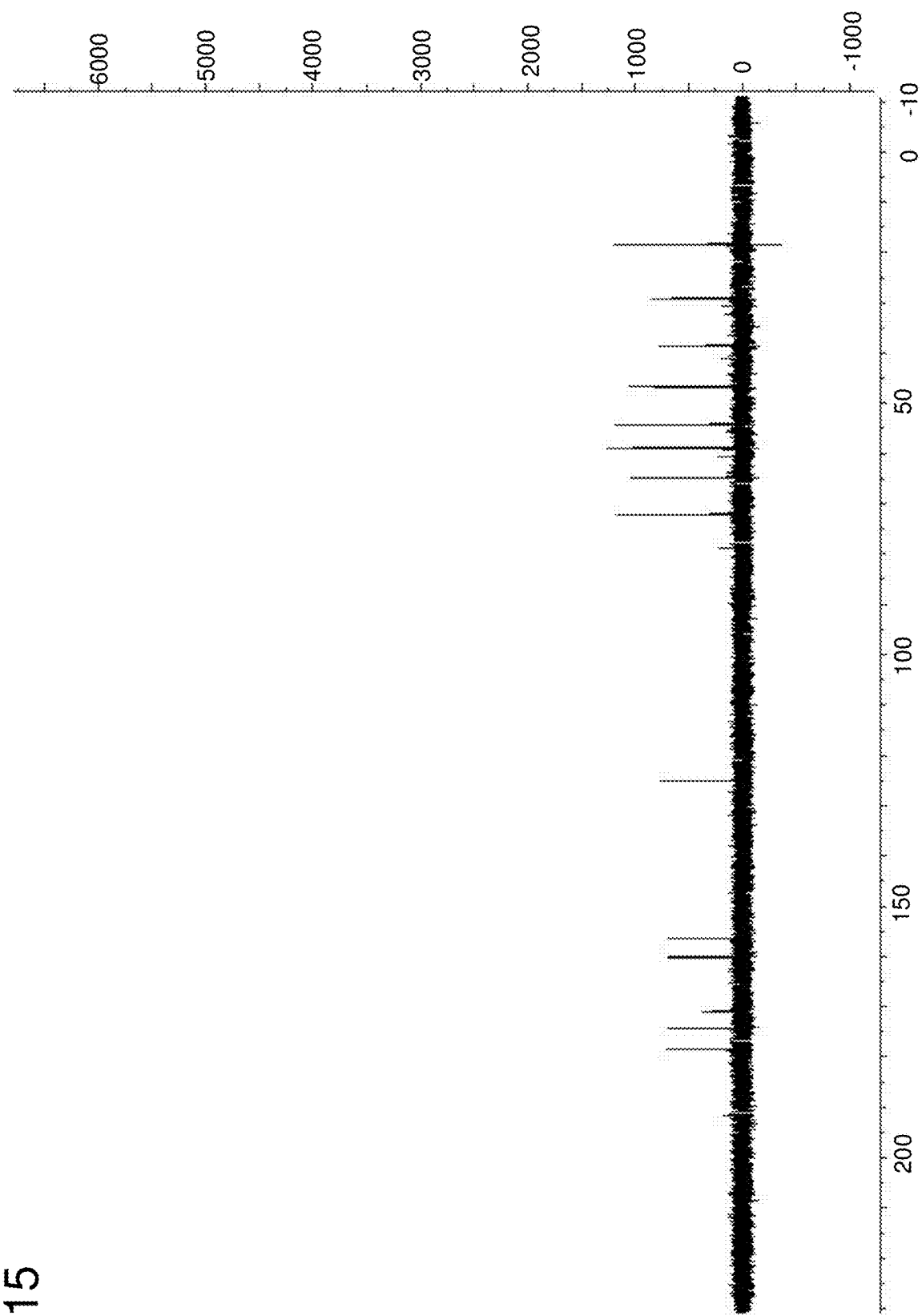
FIG. 15 depicts $^{13}$C NMR spectrum of gadusporine B. $^{13}$C NMR (176 MHz, D$_2$O) δ 178.45, 174.40, 160.19, 156.56, 125.00, 72.33, 64.77, 64.71, 58.90, 54.24, 46.72, 29.18, 18.50.
Figure 16:
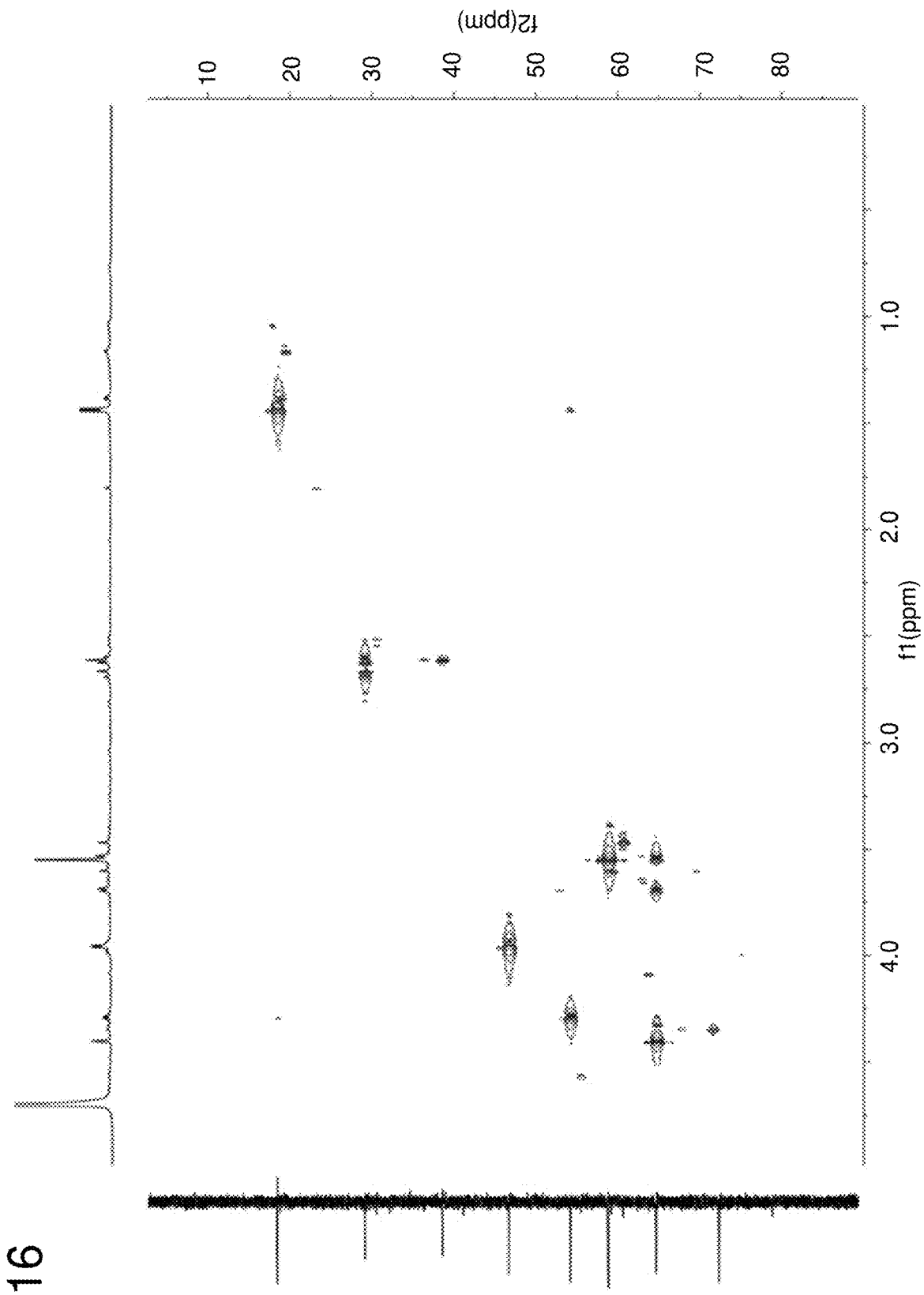
FIG. 16 depicts HSQC spectrum of gadusporine B.
Figure 17:
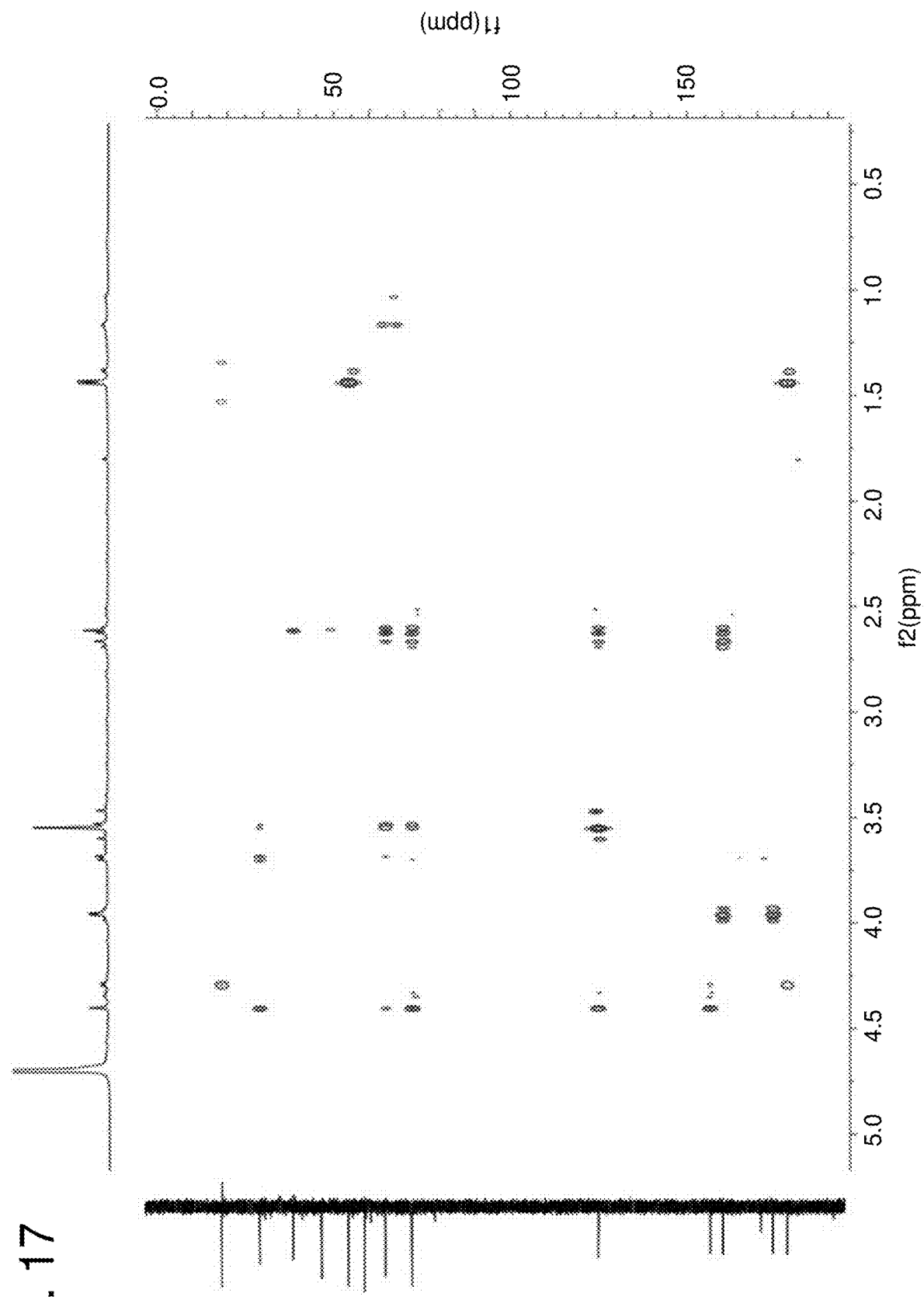
FIG. 17 depicts HMBC spectrum of gadusporine B.
Figure 18A:
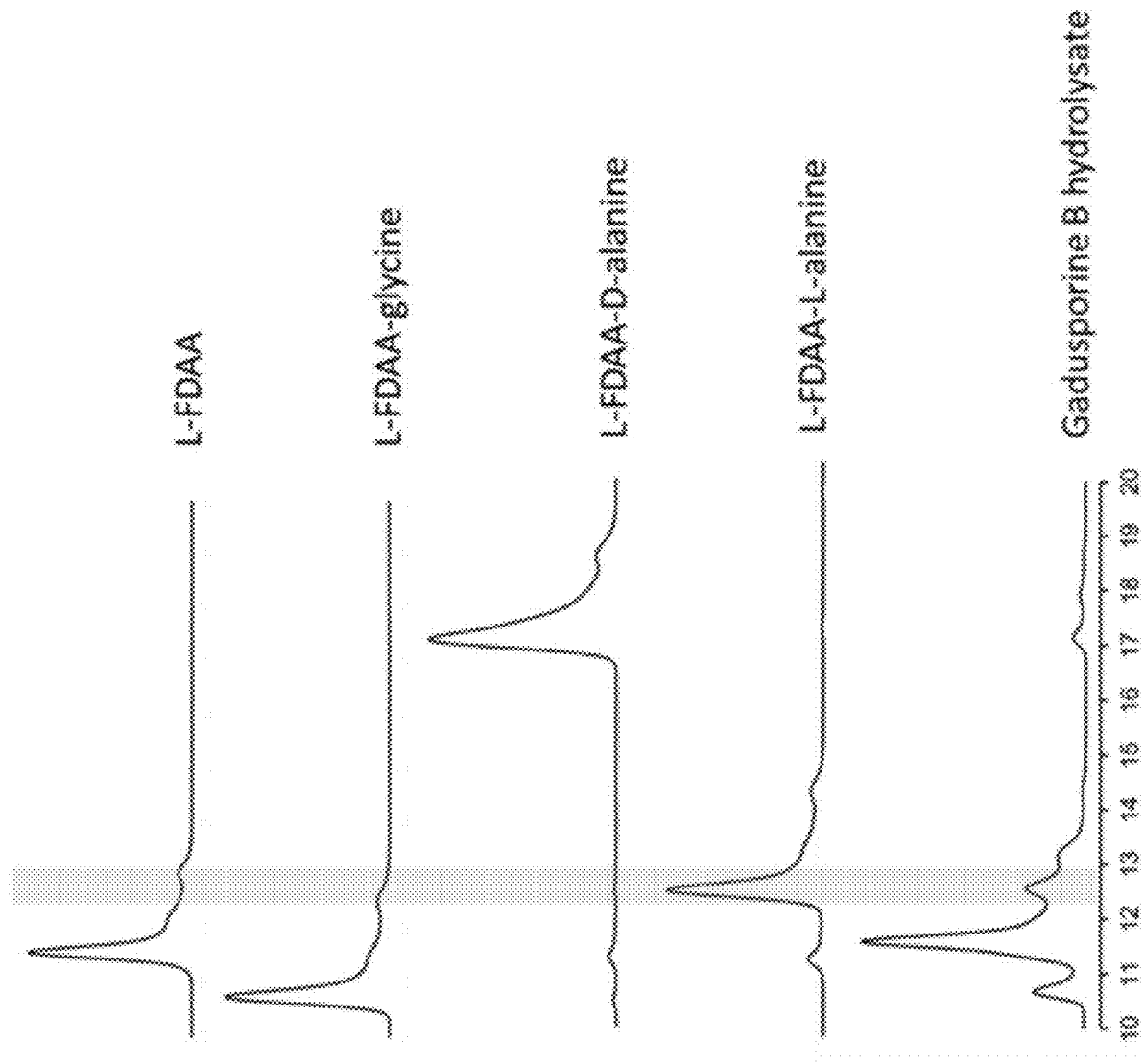
FIGS. 18A and 18B depict Marfey's analysis of gadusporine B analyzed by HPLC (FIG. 18A) and extracted ion chromatograms (EIC) confirming the HPLC Marfey's analysis results (FIG. 18B)
Figure 18B:
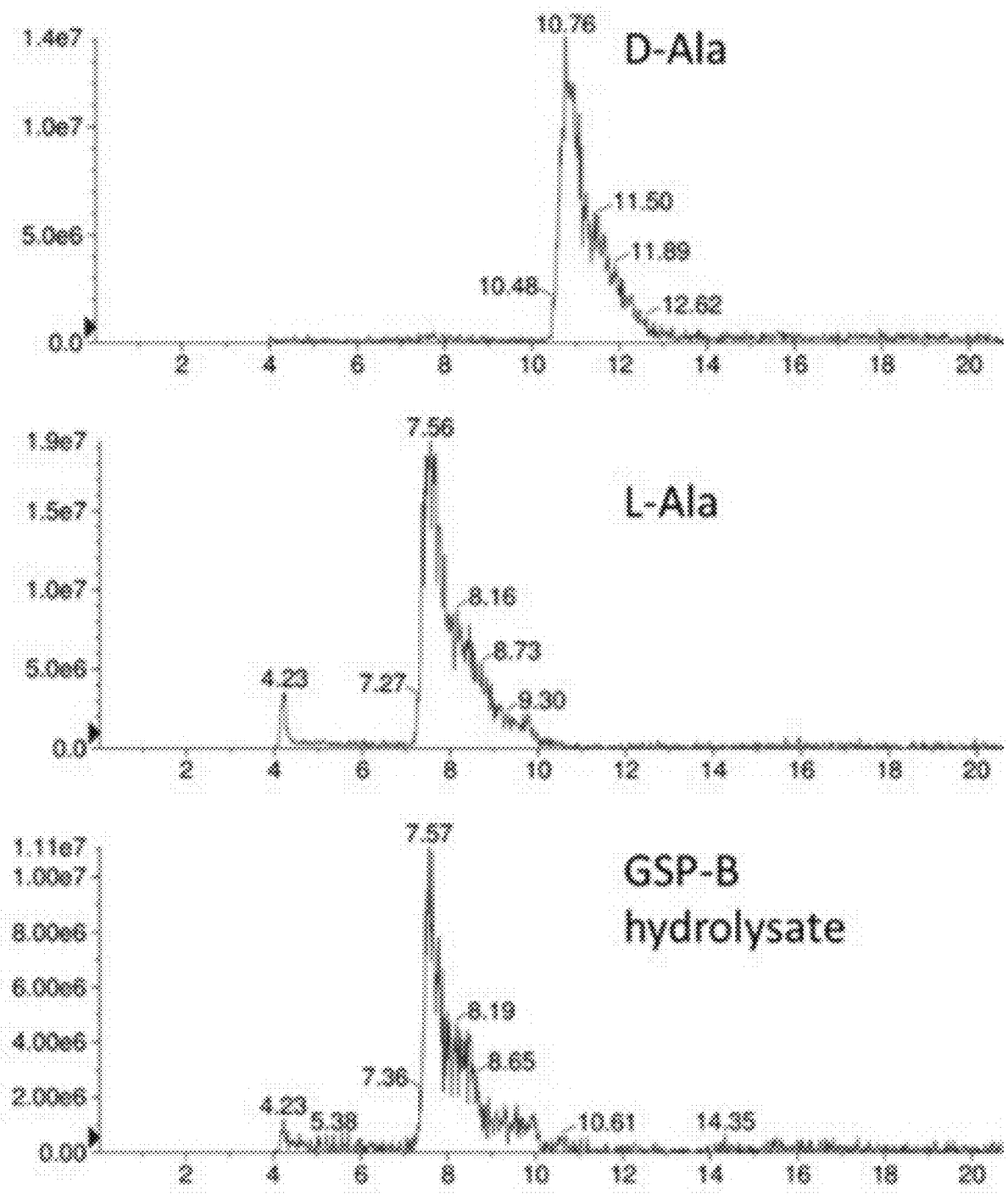

Gadusporine B was further separated from gadusol by hydrophilic interaction liquid chromatography (HILIC) (FIG. 6B). The HILIC stationary phase is critical for this separation. With zwitterionic HILIC stationary phases, gadusol and gadusporines co-eluted. Using a bare silica stationary phase, which has a negative charge due to deprotonation of the silanols, gadusporine B (positively charged at most pHs, as demonstrated with MAAs) was separated from gadusol (negatively charged at pH 7) due to cation exchange (FIG. 6B). HR-MS identified a m/z333.1290 ([M+H]$^+$), −2.1 ppm below the chemical formula $C_{13}H_{20}N_2O_8$, suggesting gadusporine B was a hydroxylated mycosporine-glycine-alanine analog (FIG. 13). NMR and Marfey's analysis (FIG. 18A) analyzed by LC-MS (see FIG. 18B for EIC) determined that gadusporine B contains L-alanine and glycine, making gadusporine B an analog of mycosporine-glycine-alanine (Table 1, FIGS. 14-17). Like gadusporine A, gadusporine B also existed in solution as a mixture of two isomers (3:1 ratio) and is not very soluble in methanol.

Figure 20:
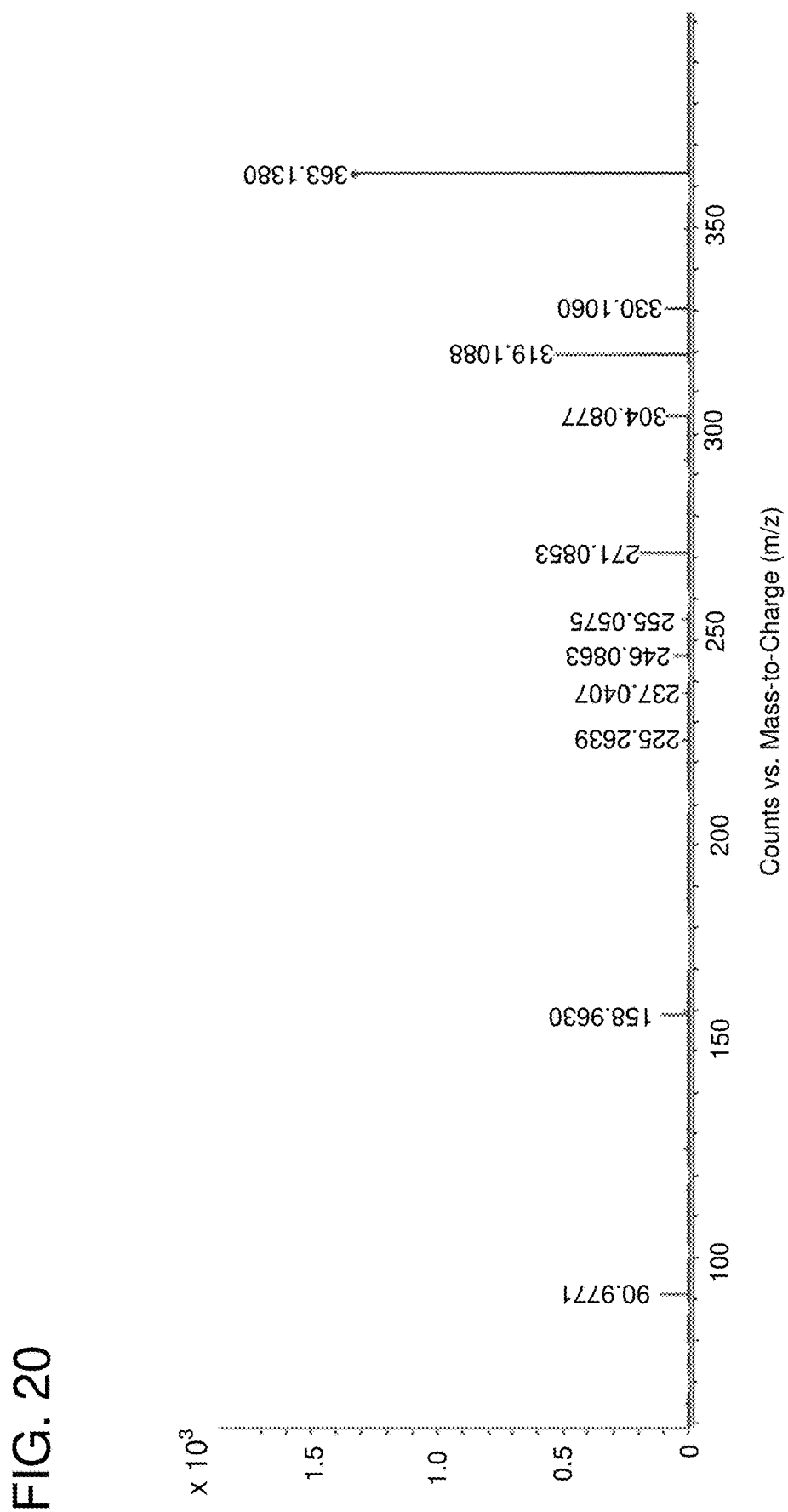
FIG. 20 depicts HR-MS fragmentation of gadusporine C.

Gadusporine C was also separated from gadusol and gadusporine B (FIG. 6B). However, there was minute amounts (<0.1 mg) and full structural elucidation, including NMR spectra, was not possible. Gadusporine C was identified by HR-MS fragmentation (FIG. 20). An ion at m/z 363.1380 ([M+H]$^+$) was identified, and was −2.3 ppm below the chemical formula of $C_{14}H_{22}N_2O_9$, the predicted formula of a hydroxylated porphyra-334 analog. The structure for gadusporine C is predicted based off the elucidated structures for gadusporines A and B (FIG. 5A).

Example 4

Sequences for Pathway Engineering

SEQ ID NO: 1 as discussed herein is a drMT-Ox mRNA transcript (NM_001013450.1) from *Danio rerio*, i.e. the wild-type protein coding sequence. SEQ ID NO: 2 is a nucleotide sequence of the valA gene (DQ164098.1) from *Streptomyces hygroscopicus*. SEQ ID NO: 3 is a codon-optimized drMT-OX nucleotide sequence from *Danio rerio* for expression in *Streptomyces*. SEQ ID NO: 4 is a mysC gene nucleotide sequence (a3L23_Rs04435) from *Rhodococcus fascians* D188. SEQ ID NO: 5 is a mysD gene nucleotide sequence (a3L23_Rs04440) from *Rhodococcus fascians* D188. SEQ ID NO: 6 is a ValA enzyme amino acid sequence from *Streptomyces hygroscopicus* (ABA41506.1). SEQ ID NO: 7 is a drMT-OX enzyme amino acid sequence from *Danio rerio*, encoded by both SEQ ID NO: 1 and SEQ ID NO: 3. SEQ ID NO: 8 is a MysC enzyme amino acid sequence (WP_032381585.1) from *Rhodococcus fascians* D188. SEQ ID NO: 9 is a MysD enzyme amino acid sequence (WP_032381584.1) from *Rhodococcus fascians* D188. Table 4 depicts a comparison of WT and synthetic sequences corresponding to SEQ ID NO: 1, 3 and 7.

TABLE 4

Comparison of WT and synthetic sequences

| Gene | WT sequence | Codon-optimized sequence |
|---|---|---|
| Mt-OX | Nucleotide sequence of ID NO: 1 | Nucleotide sequence of ID NO: 3 |
| | ATGCAGACAGCAAAAGTTTC | ATGCAGACGGCCAAGGTCTC |
| | AGACACTCCTGTGGAGTTCA | CGACACGCCCGTGGAATTCA |
| | TCGTTGAACACCTGCTGAAG | TCGTGAACACCTGCTGAAG |
| | GCAAAAGAGATCGCAGAGAA | GCGAAGGAAATCGCGGAAAA |
| | TCATGCAAGTATTCCAGTCG | CCACGCGTCGATCCCCGTGG |
| | AACTTCGGGATAATCTTCAG | AACTCCGCGACAACCTGCAG |
| | AAGGCTTTGGACATTGCTAG | AAGGCGCTCGACATCGCGTC |
| | TGGACTAGACGAATACCTTG | GGGGCTCGACGAATACCTCG |
| | AACAAATGAGCAGCAAGGAG | AACAGATGTCGAGCAAGGAA |
| | AGTGAACCGTTGACTGAGTT | TCGGAACCCCTCACGGAACT |
| | GTATAGGAAATCAGTTTCTC | CTACCGCAAGTCGGTGTCGC |
| | ATGACTGGAATAAGGTGCAT | ACGACTGGAACAAGGTGCAC |
| | GCGGACGGAAAAACCTTATT | GCGGACGGGAAGACGCTCTT |
| | TAGGCTTCCTGTTACATGCA | CCGGCTCCCCGTGACGTGTA |
| | TCACCGGACAGGTAGAAGGT | TCACGGGTCAGGTCGAAGGG |
| | CAAGTATTGAAGATGCTGGT | CAGGTGCTCAAGATGCTCGT |
| | GCATATGAGCAAAGCAAAGA | GCACATGTCGAAGGCGAAGC |
| | GGGTCTTAGAGATAGGAATG | GGGTGCTCGAAATCGGAATG |
| | TTCACAGGGTATGGGGCCTT | TTCACGGGTTACGGGGCGCT |
| | GTCAATGGCGGAGGCCTTAC | CAGCATGGCGGAAGCGCTCC |
| | CAGAAAATGGCCAGCTTATC | CGGAAAACGGTCAGCTCATC |
| | GCCTGTGAGCTTGAGCCTTA | GCGTGTGAACTCGAACCGTA |
| | CCTCAAAGACTTTGCACAGC | CCTCAAGGACTTCGCGCAGC |
| | CTATATTTGATAAATCTCCT | CCATCTTCGACAAGAGCCCC |
| | CATGGGAAAAAGATAACTGT | CACGGGAAGAAGATCACGGT |
| | GAAGACTGGGCCTGCTATGG | GAAGACGGGACCCGCGATGG |
| | ATACCCTGAAGGAATTGGCT | ACACGCTCAAGGAACTCGCG |
| | GCCACAGGAGAGCAGTTTGA | GCGACGGGTGAACAGTTCGA |
| | CATGGTATTTATTGACGCGG | CATGGTGTTCATCGACGCGG |
| | ACAAGCAGAACTACATCAAC | ACAAGCAGAACTACATCAAC |
| | TATTATAAGTTCCTCCTGGA | TACTACAAGTTCCTGCTCGA |
| | CCATAACCTTCTGCGGGATCG | CCACAACCTGCTCCGGATCG |
| | ATGGTGTTATATGTGTCGAC | ACGGTGTGATCTGTGTGGAC |
| | AACACACTGTTTAAAGGCAG | AACACGCTCTTCAAGGGTCG |
| | AGTTTACCTCAAGGACTCTG | CGTGTACCTCAAGGACTCGG |
| | TGGATGAAATGGGAAAAGCA | TCGACGAAATGGGTAAGGCG |
| | TTGCGGGATTTTAATCAGTT | CTCCGGGACTTCAACCAGTT |
| | TGTCACAGCTGATCCTCGAG | CGTGACGGCGGACCCCCGGG |
| | TAGAGCAGGTCATCATCCCT | TCGAACAGGTGATCATCCCG |
| | CTGAGAGATGGACTCACTAT | CTCCGCGACGGTCTCACGAT |
| | AATACGAAGAGTGCCCTATA | CATCCGCCGGGTGCCGTACA |
| | CACCTCAGCCAAACTCACAG | CGCCCCAGCCGAACTCGCAG |
| | AGTGGTACAGTAACCTATGA | AGCGGGACGGTGACGTACGA |
| | TGAGGTGTTTAGAGGAGTCC | CGAAGTGTTCCGGGGTGTGC |
| | AAGGAAAGCCAGTTCTGACA | AGGGGAAGCCCGTGCTCGAC |
| | AGGTTACGTTTGGATGGGAA | CGGCTCCGCCTCGACGGGAA |
| | AGTGGCCTATGTGACCGGGG | GGTGGCGTACGTCACGGGTG |
| | CCGGTCAGGGTATTGGCAGG | CGGGGCAGGGGATCGGTCGC |
| | GCTTTCGCACATGCTCTCGG | GCGTTCGCGCACGCGTCGG |
| | AGAGGCTGGAGCCAAAGTCG | TGAAGCGGGCGCGAAGGTGG |
| | CCATCATAGACATGGACAGA | CGATCATCGACATGGACCGC |
| | GGAAAGGCTGAGGATGTGGC | GGGAAGGCGGAAGACGTCGC |
| | GCATGAACTGACTTTAAAAG | GCACGAACTCACGCTCAAGG |
| | GCATTTCAAGCATGGCTGTA | GGATCAGCTCGATGGCGGTG |
| | GTGGCAGACATTAGCAAACC | GTGGCGGACATCAGCAAGCC |
| | AGACGACGTCCAGAAGATGA | CGACGACGTGCAGAAGATGA |
| | TTGACGACATCGTTACGAAA | TCGACGACATCGTGACGAAG |
| | TGGGGCACACTTCACATTGC | TGGGGCACGCTCCACATCGC |
| | TTGTAACAATGCTGGCATCA | GTGTAACAACGCGGGGATCA |
| | ACAAAAACTCAGCAAGTGAG | ACAAGAACTCGGCGTCGGAA |
| | GAGACCAGTCTAGAAGAATG | GAAACCAGCCTCGAAGAATG |
| | GGACCAAACCTTTAACGTGA | GGACCAGACGTTCAACGTGA |
| | ACCTCAGAGGCACTTTCATG | ACCTGCGGGGTACGTTCATG |
| | TGCTGCCAGGCGGCCGGTCG | TGTTGTCAGGCGGCGGGTCG |
| | TGTCATGCTGAAGCAAGGAT | CGTGATGCTCAAGCAGGGGT |
| | ACGGCAAGATAATCAACACA | ACGGGAAGATCATCAACACG |
| | GCTTCCATGGCCAGTTTAAT | GCGTCGATGGCGTCGCTCAT |
| | AGTGCCGCATCCACAGAAGC | CGTGCCGCACCCCCAGAAGC |
| | AGCTGTCCTATAACACATCC | AGCTCTCGTACAACACGTCC |
| | AAAGCTGGAGTAGTGAAACT | AAGGCGGGTGTGGTGAAGCT |
| | CACTCAAACCCTGGGCACAG | CACGCAGACGCTCGGGACGG |
| | AATGGATTGACCGAGGTGTT | AATGGATCGACCGGGAGTG |
| | CGAGTCAATTGCATCTCACC | CGCGTGAACTGTATCTCGCC |
| | TGGTATTGTTGACACCCCTC | GGGTATCGTCGACACGCCCC |
| | TCATCCATTCAGAGAGTCTG | TCATCCACACGGAATCGCTC |
| | GAGCCTCTAGTTCAGCGCTG | GAACCGCTCGTGCAGCGGTG |
| | GCTGTCAGATATCCCAGCCG | GCTCAGCGACATCCCCGCGG |
| | GACGACTGGCTCAAGCTGACA | GACGCCTCGCGCAGGTGACA |
| | GACCTCCAAGCTGCAGTGGT | GACCTGCAGGCGGCGGTCGT |
| | ATACTTGGCATCTGACGCCT | GTACCTCGCGTCGGACGCCT |
| | CTGACTACATGACAGGGCAT | CGGACTACATGACGGGACAC |
| | AACTTAGTCATAGAGGGTGG | AACCTCGTCATCGAAGGTGG |
| | TCAGAGTCTATGGTAG | GCAGTCGCTCTGGTAG |

TABLE 4-continued

Comparison of WT and synthetic sequences

| Gene | WT sequence | Codon-optimized sequence |
|---|---|---|
| Mt-OX | amino acid sequence of ID NO: 7<br>MQTAKVSDTPVEFIVEHLLK<br>AKEIAENHASIPVELRDNLQ<br>KALDIASGLDEYLEQMSSKE<br>SEPLTELYRKSVSHDWNKVH<br>ADGKTLFRLPVTCITGQVEG<br>QVLKMLVHMSKAKRVLEIGM<br>FTGYGALSMAEALPENGQLI<br>ACELEPYLKDFAQPIFDKSP<br>HGKKITVKTGPAMDTLKELA<br>ATGEQFDMVFIDADKQNYIN<br>YYKFLLDHNLLRIDGVICVD<br>NTLFKGRVYLKDSVDEMGKA<br>LRDFNQFVTADPRVEQVIIP<br>LRDGLTIIRRVPYTPQPNSQ<br>SGTVTYDEVFRGVQGKPVLD<br>RLRLDGKVAYVTGAGQGIGR<br>AFAHALGEAGAKVAIIDMDR<br>GKAEDVAHELTLKGISSMAV<br>VADISKPDDVQKMIDDIVTK<br>WGTLHIACNNAGINKNSASE<br>ETSLEEWDQTFNVNLRGTFM<br>CCQAAGRVMLKQGYGKIINT<br>ASMASLIVPHPQKQLSYNTS<br>KAGVVKLTQTLGTEWIDRGV<br>RVNCISPGIVDTPLIHSESL<br>EPLVQRWLSDIPAGRLAQVT<br>DLQAAVVYLASDASDYMTGH<br>NLVIEGGQSLW | amino acid sequence of ID NO: 7<br>MQTAKVSDTPVEFIVEHLLK<br>AKEIAENHASIPVELRDNLQ<br>KALDIASGLDEYLEQMSSKE<br>SEPLTELYRKSVSHDWNKVH<br>ADGKTLFRLPVTCITGQVEG<br>QVLKMLVHMSKAKRVLEIGM<br>FTGYGALSMAEALPENGQLI<br>ACELEPYLKDFAQPIFDKSP<br>HGKKITVKTGPAMDTLKELA<br>ATGEQFDMVFIDADKQNYIN<br>YYKFLLDHNLLRIDGVICVD<br>NTLFKGRVYLKDSVDEMGKA<br>LRDFNQFVTADPRVEQVIIP<br>LRDGLTIIRRVPYTPQPNSQ<br>SGTVTYDEVFRGVQGKPVLD<br>RLRLDGKVAYVTGAGQGIGR<br>AFAHALGEAGAKVAIIDMDR<br>GKAEDVAHELTLKGISSMAV<br>VADISKPDDVQKMIDDIVTK<br>WGTLHIACNNAGINKNSASE<br>ETSLEEWDQTFNVNLRGTFM<br>CCQAAGRVMLKQGYGKIINT<br>ASMASLIVPHPQKQLSYNTS<br>KAGVVKLTQTLGTEWIDRGV<br>RVNCISPGIVDTPLIHSESL<br>EPLVQRWLSDIPAGRLAQVT<br>DLQAAVVYLASDASDYMTGH<br>NLVIEGGQSLW |

In this way, a genetic mix-and-match pathway engineering approach enabled production of hybrid analogs of gadusol and mycosporines. The hybrid analogs have herein been termed gadusporines. A technical effect of combining biosynthetic genes from different organisms (which may include those from different kingdoms), can lead to the production of novel natural product analogs.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A synthetic gene cluster, comprising:
   a valA nucleotide sequence capable of expressing ValA;
   a nucleotide sequence capable of expressing methyltransferase/oxidoreductase (MT-Ox) protein;
   a mysC nucleotide sequence capable of expressing a MysC protein; and
   a mysD nucleotide sequence capable of expressing a MysD protein.

2. The synthetic gene cluster of claim 1, wherein the valA nucleotide sequence is from *Streptomyces hygroscopicus*.

3. The synthetic gene cluster of claim 2, wherein the valA nucleotide sequence encodes a protein that is at least 95% identical to SEQ ID NO: 6.

4. The synthetic gene cluster of claim 2, wherein the valA nucleotide sequence is at least 95% identical to SEQ ID NO: 2.

5. The synthetic gene cluster of claim 1, wherein the nucleotide sequence capable of expressing methyltransferase/oxidoreductase (MT-Ox) protein is a drMT-Ox nucleotide sequence from *Danio rerio*.

6. The synthetic gene cluster of claim 5, wherein the drMT-Ox nucleotide sequence encodes a protein that is at least 95% identical to SEQ ID NO: 7.

7. The synthetic gene cluster of claim 5, wherein the drMT-Ox nucleotide sequence is at least 95% identical to SEQ ID NO: 3.

8. The synthetic gene cluster of claim 1, wherein the mysC nucleotide sequence is from *Rhodococcus fascians* D188.

9. The synthetic gene cluster of claim 8, wherein the mysC nucleotide sequence encodes a protein that is at least 95% identical to SEQ ID NO: 8.

10. The synthetic gene cluster of claim 8, wherein the mysC nucleotide sequence is at least 95% identical to SEQ ID NO: 4.

11. The synthetic gene cluster of claim 1, wherein the mysD nucleotide sequence is from *Rhodococcus fascians* D188.

12. The synthetic gene cluster of claim 11, wherein the mysD nucleotide sequence encodes a protein that is at least 95% identical to SEQ ID NO: 9.

13. The synthetic gene cluster of claim 11, wherein the mysD nucleotide sequence is a least 95% identical to SEQ ID NO: 5.

14. A bacterium with an expression vector with a synthetic gene cluster comprising:
   a valA nucleotide sequence capable of expressing ValA;
   a nucleotide sequence capable of expressing methyltransferase/oxidoreductase (MT-Ox) protein;
   a mysC nucleotide sequence capable of expressing a MysC protein; and
   a mysD nucleotide sequence capable of expressing a MysD protein.

15. The bacterium of claim 14, having the accession number PTA-126147.

16. The bacterium of claim 14, wherein the valA nucleotide sequence is at least 95% identical to SEQ ID NO: 2, wherein the nucleotide sequence capable of expressing methyltransferase/oxidoreductase (MT-Ox) protein is a drMT-Ox nucleotide sequence and the drMT-Ox nucleotide sequence is at least 95% identical to SEQ ID NO: 3, the mysC nucleotide sequence is at least 95% identical to SEQ ID NO: 4; and the mysD nucleotide sequence is a least 95% identical to SEQ ID NO: 5.

17. A method of producing one or more gadusol functional derivatives, comprising,
   culturing a host cell having an expression vector with the synthetic gene cluster of claim 1; and
   isolating the one or more functional gadusol derivatives from the culture.

18. The method of claim 17, wherein the host cell is a *S. coelicolor* cell.

19. The method of claim 17, wherein the nucleotide sequence is at least 95% identical to SEQ ID NO: 2, wherein the nucleotide sequence capable of expressing methyltransferase/oxidoreductase (MT-Ox) protein is a drMT-Ox nucleotide sequence and the drMT-Ox nucleotide sequence is at least 95% identical to SEQ ID NO: 3, the mysC nucleotide sequence is at least 95% identical to SEQ ID NO: 4; and the mysD nucleotide sequence is a least 95% identical to SEQ ID NO: 5.

* * * * *

SEQUENCE LISTING

```
Sequence total quantity: 9
SEQ ID NO: 1           moltype = RNA   length = 1656
FEATURE                Location/Qualifiers
source                 1..1656
                       mol_type = mRNA
                       organism = Danio rerio
SEQUENCE: 1
atgcagacgg ccaaggtctc cgacacgccc gtggaattca tcgtggaaca cctgctgaag    60
gcgaaggaaa tcgcggaaaa ccacgcgtcg atccccgtgg aactccgcga caacctgcag   120
aaggcgctcg acatcgcgtc ggggctcgac gaataccctcg aacagatgtc gagcaaggaa   180
tcggaacccc tcacggaact ctaccgcaag tcggtgtcgc acgactggaa caaggtgcac   240
gcggacggga agacgctctt ccggctcccc gtgacgtgta tcacgggtca ggtcgaaggg   300
caggtgctca agatgctcgt gcacatgtcg aaggcgaagc gggtgctcga aatcgggatg   360
ttcacgggtt acggggcgct cagcatggcg gaagcgctcc cggaaaacgg tcagctcatc   420
gcgtgtgaac tcgaaccgta cctcaaggac ttcgcgcagc ccatcttcga caagagcccc   480
cacggaaga  agatcacggt gaagacggga cccgcgatgg acacgctcaa ggaactcgcg   540
gcgacgggtg aacagttcga catggtgttc atcgacgcgg acaagcaaa ctacatcaac   600
tactacaagt tcctgctcga ccacaacctg ctccggatcg acggtgtgat ctgtgtggac   660
aacacgctct tcaagggtcg cgtgtacctc aaggactcgg tcgacgaaat gggtaaggcg   720
ctccgggact tcaaccagtt cgtgacggcg gaccccgggg tcgaacaggt gatcatcccg   780
ctccgcgacg gtctcacgat catccgccgg gtgccgtaca cgccccagcc gaactcgcag   840
agcgggacgg tgacgtacga cgaagtgttc cggggtgtgc aggggaagcc cgtgctcgac   900
cggctccgcc tcgacgggaa ggtggcgtac gtcacgggtg cggggcaggg gatcggtcgc   960
gcgttcgcgc acgcgctcgg tgaagcgggc gcgaaggtgg cgatcatcga catggaccgc  1020
gggaaggcgg aagacgtcgc gcacgaactc acgctcaagg ggatcagctc gatggcggtg  1080
gtggcggaca tcagcaagcc cgacgacgtg cagaagatga tcgacgacat cgtgacgaag  1140
tggggcacgc tccacatcgc gtgtaacaac gcggggatca acaagaactc ggcgtcggaa  1200
gaaaccagcc tcgaagaatg ggaccagacg ttcaacgtga acctgcgggg tacgttcatg  1260
tgttgtcagg cggcgggtcg cgtgatgctc aagcaggggt acgggaagat catcaacacg  1320
gcgtcgatgg cgtcgctcat cgtgccgcac ccccagaagc agctctcgta caacacgtcc  1380
aaggcgggtg tggtgaagct cacgcagacg ctcgggacgg aatggatcga ccggggagtg  1440
cgcgtgaact gtatctcgcc gggtatcgtc gacacgcccc tcatccacag cgaatcgctc  1500
gaaccgctcg tgcagcggtg gctcagcgac atccccgcgg gacgcctcgc gcaggtgacg  1560
gacctgcagg cggcggtcgt gtacctcgcg tcggacgcct cggactacat gacgggacac  1620
aacctcgtca tcgaaggtgg gcagtcgctc tggtag                             1656

SEQ ID NO: 2           moltype = DNA   length = 1245
FEATURE                Location/Qualifiers
source                 1..1245
                       mol_type = genomic DNA
```

```
                     organism = Streptomyces hygroscopicus
SEQUENCE: 2
atgaccatga ccaagcagag ttccttatcc cccggtagcc gcctgtacga ctacaccacg   60
caggacggcg cggcctggcg ggtgagcgcg ctcaaggagg tgagctacga cgtcgtggtg  120
cagccggccg tgctcgatcc ggcgaatccg cgctcgacg acgccctctc gtccgggacg  180
acgcctgcgc gccggctcat cgtcatagac gctacggtgc gctccctcta cggcgagcag  240
cttgccgcct acctggcggg ccatgacgtg gagttccacc tgtgcgtcat cgacgcacac  300
gagtcggcaa aggtcatgga gaccgtcttc gaagtcgtgg acgcgatgga cgccttcggt  360
gtgccacggc gccacgcgcc ggtgctcgcc atgggtggcg gggtgctcac ggacatcgtc  420
ggtcttgcgg cgagcctgta ccgcagggcc acgccgtacg tccgcatacc cacgacccg   480
atcgggatga tcgacgcggg catcggcgcc aagacaggtg tcaacttccg tgagcacaag  540
aatcggttgg gcacgtatca ccctcctcg ctgaccctca tcgatcccgg cttcctcgcc  600
acactcgacg cccgacacct gcgcaacggt ctggcggaaa tcctgaaggt agccctggtc  660
aaggatgccg aactgttcga tctgctggag gggcacgggc ggagcctggt cgagcagcgg  720
atgcaaccgg gcgagggcgg gacgggcggt gcggcgctca cagtgttgcg ccgggcggtc  780
cagggcatgc tggaggagct ccagcccaat ctctgggaac accagctgcg gcgcctggtg  840
gacttcggcc actccttctc acccagcgtg agatggcgg cgctgccga gttgctgcac  900
ggcgaggccg tctgcatcga catgggcgctc agctcggtgc tcgcccacca ccgtgggcta  960
ctgaccgagg ccgagctcgg ccgtgtcctc gatgtcatgc gtctgctcca cctgcctgta 1020
cttcacccgg tgtgcacgcc ggacctcatg cgccggcgc tcgcggacac ggtcaaacac 1080
cgggacggct ggcaacacat gcccttcca cgcgggatcg gcgacgccgt gttcgtgaac 1140
gacgtcactc aacgggagat cgaggccgcg cttctcacac tcgccgagcg ggaccgggtg 1200
ccgcggtggc gggcgctgca cggtgccgtg gacatggggg tgtga              1245

SEQ ID NO: 3              moltype = DNA   length = 1656
FEATURE                   Location/Qualifiers
misc_feature              1..1656
                          note = methyltransferase-oxidoreductase (MT-Ox) sequence
                            from Danio rerio, codon optimized for expression in
                            Streptomyces
source                    1..1656
                          mol_type = other DNA
                          organism = synthetic construct
SEQUENCE: 3
atgcagacgg ccaaggtctc cgacacgccc gtggaattca tcgtggaaca cctgctgaag   60
gcgaaggaaa tcgcgaaaaa ccacgcgtcg atccccgtgg aactccgcga caacctgcag  120
aaggcgctcg acatcgcgtc ggggctcgac gaataccctcg aacagatgtc gagcaaggaa  180
tcggaacccc tcacggaact ctaccgcaag tcggtgtcgc acgactggaa caaggtgcac  240
gcggacggga agacgctctt ccggctcccc gtgacgtgta tcacgggtca ggtcgaaggg  300
caggtgctca agatgctcgt gcacatgtcg aaggcgaagc gggtgctcga atcggaatgc  360
ttcacgggtt acggggcgct cagcatgcg gaagcgctcc cggaaaacgg tcagctcatc  420
gcgtgtgaac tcgaaccgta cctcaaggac ttcgcgcagc catcttcga caagagcccc  480
cacgggaact agatcacggt gaagacggga cccgcgcaa ggaactcgtg ggaacctcgg  540
gcgacgggtg aacagttcga catggtgttc atcgacgcgg acaagcagaa ctacatcaac  600
tactacaagt tcctgctcga ccacaacctg ctccggatcg acgtgtgat ctgtgtggac  660
aacacgctct tcaagggtcg cgtgtacctc aaggactcgg tcgacgaaat gggtaaggcg  720
ctccggact tcaaccagtt cgtgacggcg gaccccccgg tcgaacaggt gatcatcccg  780
ctccgcgacg gtctcacgat catccgccgg gtgccgtaca cgccccagcc gaactcgcag  840
agcgggacgg tgacgtacga cgaagtgttc cggggtgtgc agggggaagcc cgtgctcgac  900
cggctccgcc tcgacgggaa ggtggcgtac gtcacggtg cgggcaggg gatcggtcgc  960
gcgttcgccgc acgcgctcgg tgaagcgggc gcgaaggtgg cgatcatcga catggaccgc 1020
gggaaggcgg aagacgtcgc gcacgaactc acgctcaagg ggatcagctc gatgcggtgt 1080
gtggcggaca tcagcaagcc cgacgacgtg cagaagatga tcgacgacat cgtgacgaag 1140
tggggcacgc tccacatcgc gtgtaacaac gcggggatca acaagaactc ggcgtcggaa 1200
gaaaccagcc tcgaagaatg ggaccacacg ttcaacgtga acctgcgggg tacgttcatg 1260
tgttgtcagg cggcgggtcg cgtgatgctc aagcagggt acgggaagat catcaacacg 1320
gcgtcgatgg cgtcgctcat cgtgccgcac cccagaagc agctctcgta caacacgtcc 1380
aaggcgggtg tggtgaagct cacgcagacg ctcgggacgg aatggatcga ccggggagtg 1440
cgcgtgaact gtatctcgcc gggtatcgtc gacacgcccc tcatccacag cgaatcgctc 1500
gaaccgctcg tgcagcggtg gctcagcgac atccccgcgg gacgcctcgc gcaggtgacg 1560
gacctgcagg cggcggtcgt gtacctcgcg tcggacgcct cggactacag gacgggacac 1620
aacctcgtca tcgaaggtgg gcagtcgctc tggtag                           1656

SEQ ID NO: 4              moltype = DNA   length = 1287
FEATURE                   Location/Qualifiers
source                    1..1287
                          mol_type = genomic DNA
                          organism = Rhodococcus fascians
SEQUENCE: 4
atgatccgca ccgtcgcggc gctgatcggc ctcacggtca ccctcccgt cgacctcgcg   60
gcggtggggg tggcggcgct gagaggtacc cggcccgccg cccatcgaac cgattcgccc  120
agaacgattc tgatcagtgg cggaaagatg accaaagcct tgcaactcgc acggtccttc  180
catctcgccg gccatcgggt gatcctcgtg aatcggcga agtaccgctg gaccggacat  240
cgtttctccc gcgctgtcga ccgttttccat tgccgttcccg accgggtga ttcgggatat  300
gcgcaggctc tgctggacat cgtcgccgc gagggctcg acgtcttcgt gcccgtgca   360
agcccggctg cgagtattca cgacgccgac gcgcgtgcac cctcgatgc gcactgcgag  420
gtgatccacg cgacgcggga taccgtacgg atggtcgacg acaagtcccg attctccgag  480
cacgcagcgt cattgggact ccgggttccc gacttcaagc gcatcaccga ccccgcccag  540
atcgacgaat cgacttcgc gccggccgt gagtacatcc tcaaacggat ctcgtacaac  600
```

```
ccggtcggcc gaatggatct gacgcgttg acggcgcaca cgccggaacg caactcctcg   660
ttcgcccgga gcctgcacat caccgagaac gacccgtgga tcctgcagga attcatcgcc   720
ggacaggagt actgcacgca cggcacggtt cgcgagggtc gcctgcaggt gtacggctgc   780
tgcgtgtcgt ccgccttcca ggtcaactac gagatggtgg acaagcccga aatcctgtgc   840
tgggtagaga cattcgtctc ctcgctcgac accaccggac agctgtcgtt cgacttcatc   900
gagtccgccg ccgacggccg gatctacgcc atcgaatgca acccgcgcac ccactcggcc   960
atcacgatgt tctacgacca ccccgacctg gctgccgcgt acctcgacga cgggcatgcc  1020
gagatcgtgc cgcgtgcgac ggcccggccg acgtactgga tctaccacga gctgtggcgt  1080
ctgatcaccg agggtgatcg agtatctcgg ctccgcacca tctttcgagg caaggacgcc  1140
atcctcaccg gttgggatcc cctgccgtat ctgttggtac atcatcttca gattccgtcg  1200
ttgctgatcc ggaacctccg cgagcggcgt ggctggtccc gaatcgattt caacatcggc  1260
aaactcgtgg aaaacggagg cgactga                                      1287

SEQ ID NO: 5            moltype = DNA  length = 1026
FEATURE                 Location/Qualifiers
source                  1..1026
                        mol_type = genomic DNA
                        organism = Rhodococcus fascians
SEQUENCE: 5
atgacgttgt cggtcgtggt gctcgtcggg tcctcggtgg accgctttca cagtgatctc    60
tctcgggtct acgccggcgg cttcctgggt gccctcggta cgaccccgc gtacggtttc    120
gagatcgcgt tcgtctctcc cggcggcctc tggagtttcc ccaccgatct cgaggattcg   180
agtatcgctg cggcgcagca gatgccgttg gcacaggcgg tggagcacat tgcggtgcga   240
gacttcgacg tcatggttcc gcagatgttc tgcctgccgg gtatgacgac gtaccgcagc   300
ctgttcgatc tactgggcgt gccctacccc ggcaacggtc cggacctgat ggcgttgacg   360
gcgaacaagg cccgcgcccg cgcagtcgtc gcggcgacgc cgtcgtgt tcccgacgtg   420
gtggtcgtcc gatccgccga cgacgtgatg gacctcgccc tgccggtcgt ggtcaagccc   480
gtggattccg acaactcgat gggtgtctcg ctggtccacg agtccgacgg gctggcaccc   540
gcgattcgag aggctctgac gtattcgtct gcggcactgg tggagacgta cgttccactg   600
ggtcgtgaag ttcggtcgg gatcatcgtc cgagatgcga aacttcgtcg cttgcccctc   660
gaggagtacg ccgtcgactc cgtccgcagt agtgcggaca agctgaatcg cacatccgac   720
ggcgatctct acctggtggc gaaagagcag accagagcct ggacggtcga cgtcacggat   780
ccgatcaccg aaaaagtctg gcagcagca cgatcgagtc acatcgcact gggatgtcgg   840
cactacggcc tgttcgactt ccgcatcgac ccggacggcg agccgtggtt tctcgaagcc   900
agcctctact gctcctattc gccgtccagc gtgttggcgg tgatgccgc ggccgcgggc   960
atcaccgtcg aagatttgtt cgcattcgcg ctcgaagaac tgccggtgaa ggagtcgtcg  1020
tcatga                                                              1026

SEQ ID NO: 6            moltype = AA  length = 414
FEATURE                 Location/Qualifiers
source                  1..414
                        mol_type = protein
                        organism = Streptomyces hygroscopicus
SEQUENCE: 6
MTMTKQSSLS PGSRLYDYTT QDGAAWRVSA LKEVSYDVVV QPRLLDPANP ALADALSSGT    60
TPARRLIVID ATVRSLYGEQ LAAYLAGHDV EFHLCVIDAH ESAKVMETVF EVVDAMDAFG   120
VPRRHAPVLA MGGGVLTDIV GLAASLYRRA TPYVRIPTLL IGMIDAGIGA KTGVNFREHK   180
NRLGTYHPSS LTLIDPGFLA TLDARHLRNG LAEILKVALV KDAELFDLLE GHGASLVEQR   240
MQPGEGGTGG AALTVLRRAV QGMLEELQPN LWEHQLRRLV DFGHSFSPSV EMAALPELLH   300
GEAVCIDMAL SSVLAHHRGL LTEAELGRVL DVMRLLHLPV LHPVCTPDLM RAALADTVKH   360
RDGWQHMPLP RGIGDAVFVN DVTQREIEAA LLTLAERDRV PRWRALHGAV DMGV         414

SEQ ID NO: 7            moltype = AA  length = 551
FEATURE                 Location/Qualifiers
source                  1..551
                        mol_type = protein
                        organism = Danio rerio
SEQUENCE: 7
MQTAKVSDTP VEFIVEHLLK AKEIAENHAS IPVELRDNLQ KALDIASGLD EYLEQMSSKE    60
SEPLTELYRK SVSHDWNKVH ADGKTLFRLP VTCITGQVEG QVLKMLVHMS KAKRVLEIGM   120
FTGYGALSMA EALPENGQLI ACELEPYLKD FAQPIFDKSP HGKKITVKTG PAMDTLKELA   180
ATGEQFDMVF IDADKQNYIN YYKFLLDHNL LRIDGVICVD NTLFKGRVYL KDSVDEMGKA   240
LRDFNQFVTA DPRVEQVIIP LRDGLTIIRR VPYTPQPNSQ SGTVTYDEVF RGVQGKPVLD   300
RLRLDGKVAY VTGAGQGIGR AFAHALGEAG AKVAIIDMDR GKAEDVAHEL TLKGISSMAV   360
VADISKPDDV QKMIDDIVTK WGTLHIACNN AGINKNSASE ETSLEEWDQT FNVNLRGTFM   420
CCQAAGRVML KQGYGKIINT ASMASLIVPH PQKQLSYNTS KAGVVKLTQT LGTEWIDRGV   480
RVNCISPGIV DTPLIHSESL EPLVQRWLSD IPAGRLAQVT DLQAAVVYLA SDASDYMTGH   540
NLVIEGGQSL W                                                        551

SEQ ID NO: 8            moltype = AA  length = 428
FEATURE                 Location/Qualifiers
source                  1..428
                        mol_type = protein
                        organism = Rhodococcus fascians
SEQUENCE: 8
MIRTVAALIG LTVTLPVDLA AVGVAALRGT RPAAHRTDSP RTILISGGKM TKALQLARSF    60
HLAGHRVILV ESAKYRWTGH RFSRAVDRFH CVPDPGDSGY AQALLDIVRR EGVDVFVPVA   120
SPAASIHDAD ARALLDAHCE VIHGDADTVR MVDDKSRFSE HAASLGLRVP DFKRITDPAQ   180
IDEFDFAPGR EYILKRISYN PVGRMDLTRL TAHTPERNSS FARSLHITEN DPWILQEFIA   240
```

```
GQEYCTHGTV REGRLQVYGC CVSSAFQVNY EMVDKPEILC WVETFVSSLD TTGQLSFDFI    300
ESAADGRIYA IECNPRTHSA ITMFYDHPDL AAAYLDDGHA EIVPRATARP TYWIYHELWR    360
LITEGDRVSR LRTIFRGKDA ILTGWDPLPY LLVHHLQIPS LLIRNLRERR GWSRIDFNIG    420
KLVENGGD                                                            428

SEQ ID NO: 9           moltype = AA  length = 341
FEATURE                Location/Qualifiers
source                 1..341
                       mol_type = protein
                       organism = Rhodococcus fascians
SEQUENCE: 9
MTLSVVVLVG SSVDRFHSDL SRVYAGGFLG ALGNDPAYGF EIAFVSPGGL WSFPTDLEDS     60
SIAAAQQMPL AQAVEHIAVR DFDVMVPQMF CLPGMTTYRS LFDLLGVPYP GNGPDLMALT    120
ANKARARAVV AAAGVRVPDG VVVRSADDVM DLALPVVVKP VDSDNSMGVS LVHESDGLAP    180
AIREALTYSS AALVETYVPL GREVRCGIIV RDGELACLPL EEYAVDSVRS SADKLNRTSD    240
GDLYLVAKEQ TRAWTVDVTD PITEKVWAAA RSSHIALGCR HYGLFDFRID PDGEPWFLEA    300
SLYCSYSPSS VLAVMAAAAG ITVEDLFAFA LEELPVKESS S                        341
```